(12) United States Patent
Yamauchi et al.

(10) Patent No.: US 10,408,842 B2
(45) Date of Patent: Sep. 10, 2019

(54) SUBCELLULAR WESTERN BLOTTING OF SINGLE CELLS

(71) Applicant: The Regents of the University of California, Oakland, CA (US)

(72) Inventors: Kevin A. Yamauchi, Berkeley, CA (US); Amy E. Herr, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 289 days.

(21) Appl. No.: 15/310,065

(22) PCT Filed: May 29, 2015

(86) PCT No.: PCT/US2015/033375
§ 371 (c)(1),
(2) Date: Nov. 9, 2016

(87) PCT Pub. No.: WO2015/184386
PCT Pub. Date: Dec. 3, 2015

(65) Prior Publication Data
US 2017/0242020 A1     Aug. 24, 2017

Related U.S. Application Data

(60) Provisional application No. 62/005,848, filed on May 30, 2014.

(51) Int. Cl.
*G01N 27/447* (2006.01)
*G01N 33/68* (2006.01)
(Continued)

(52) U.S. Cl.
CPC .......... *G01N 33/6803* (2013.01); *C07K 1/26* (2013.01); *G01N 27/44747* (2013.01);
(Continued)

(58) Field of Classification Search
CPC .......... G01N 27/447; G01N 27/44743; G01N 27/44747; C12Q 2565/125; C12N 15/101
See application file for complete search history.

(56) References Cited

U.S. PATENT DOCUMENTS 3,964,992 A    6/1976  Krotz
6,664,047 B1 * 12/2003 Haugland ............... C09B 23/02
                                                    435/29
(Continued)

FOREIGN PATENT DOCUMENTS

EP         1813938 A1 *  1/2006  ........... G01N 27/447
WO         2014138475     9/2014

OTHER PUBLICATIONS

Narayanan et al., "Determination of agarose gel pore size: Absorbance measurements vis a vis other techniques," Journal of Physics: Conference Series 28 (2006) 83-86 (Year: 2006).*
(Continued)

*Primary Examiner* — Alexander S Noguerola
(74) *Attorney, Agent, or Firm* — Rudy J. Ng; Bozicevic, Field & Francis LLP

(57) ABSTRACT

Electrophoretic separation methods and systems for performing the same are provided. The methods and systems find use in a variety of different electrophoretic separation applications, such as sub-cellular Western blotting of single cells.

19 Claims, 4 Drawing Sheets

(51) Int. Cl.
*C07K 1/26* (2006.01)
*G01N 33/543* (2006.01)
*G01N 33/545* (2006.01)
*G01N 33/561* (2006.01)
*C12N 15/10* (2006.01)

(52) U.S. Cl.
CPC ..... *G01N 27/44791* (2013.01); *G01N 33/545* (2013.01); *G01N 33/54306* (2013.01); *G01N 33/561* (2013.01); *C12N 15/101* (2013.01); *C12Q 2565/125* (2013.01); *G01N 27/44756* (2013.01); *G01N 2550/00* (2013.01); *G01N 2570/00* (2013.01)

(56) References Cited

U.S. PATENT DOCUMENTS

| 6,905,585 | B2* | 6/2005 | Goncalves | G01N 27/44704 |
| | | | | 204/466 |
| 2011/0028339 | A1 | 2/2011 | Jones et al. | |
| 2011/0177618 | A1 | 7/2011 | Herr et al. | |
| 2012/0277118 | A1* | 11/2012 | Bhatia | B01L 3/502715 |
| | | | | 506/10 |
| 2012/0329040 | A1 | 12/2012 | Herr et al. | |
| 2013/0069000 | A1* | 3/2013 | Anupama | A61L 15/60 |
| | | | | 252/194 |

OTHER PUBLICATIONS

Hughes et al., "Microfluidic Western blotting," PNAS Dec. 26, 2012, vol. 109, No. 52, pp. 21450-21455 plus Supporting Information, five pages (Year: 2012).*

Set of presentation slides by Caitlin Buckspan entitled "Western Blot—An Introduction to Western Blotting Principles and Troubleshooting," abcam®, Feb. 15, 2011. Downloaded from http://docs.abcam.com/pdf/events/Western-blot-webinar-presentation.pdf (Year: 2011).*

Hughes et al., (2013) "Single Cell Western Blotting," 17th International Conference on Miniaturized Systems for Chemistry and Life Sciences 2: 1338-1340 XP009500600.

Sawasdilchai et al (2010) "In situ Subcellular Fractionation of Adherent and Non-adherent Mammalian Cells," Journal of Visualized Experiments 1-5 XP055413676.

Shaiken et al.(2014) "Dissecting the cell to nucleus, perinucleus and cytosol," Scirntific Reports 4(1): 1-10 XP055413680.

* cited by examiner

US 10,408,842 B2

SUBCELLULAR WESTERN BLOTTING OF SINGLE CELLS

CROSS-REFERENCE TO RELATED APPLICATION

Pursuant to 35 U.S.C. § 119(e), this application claims priority to the filing date of U.S. Provisional Application No. 62/005,848, filed May 30, 2014, the disclosure of which is incorporated herein by reference.

REFERENCE TO GOVERNMENT SUPPORT

This invention was made with government support under grant number OD007294 awarded by the National Institutes of Health. The government has certain rights in the invention.

INTRODUCTION

A variety of analytical techniques may be used to separate and detect specific analytes in a given sample. A range of related immunoblotting methods have enabled the identification and semi-quantitative characterization of e.g., DNA (Southern blot), RNA (northern blot), proteins (Western blot), and protein-protein interactions (far-western blot); by coupling biomolecule separations and assays. For example, Western blotting can be used to detect proteins in a sample by using gel electrophoresis to separate the proteins in the sample followed by probing with antibodies specific for the target protein. In a typical Western blot, gel electrophoresis is used to separate native proteins by 3-D structure or denatured proteins by the length of the polypeptide. The proteins are then transferred to a membrane (typically nitrocellulose or PVDF), where they are probed (detected) using antibodies specific to the target protein.

Proteomic analysis of rare cell populations may be challenging due to very low cell concentrations in an analysis sample. For example, circulating tumor cells may be present at 1-10 cells per mL of blood, and may not be suitable for conventional assays (e.g., western blots and flow cytometry), which require ~$10^6$ cells for accurate results. Additionally, the analysis of a large cell population can obscure sub-populations that behave differently than the average. Cell-to-cell variability can lead to different outcomes, and thus the study of individual cell behavior may be performed by single-cell analysis.

SUMMARY

Electrophoretic separation methods and systems for performing the same are provided. Aspects of embodiments of the present disclosure include a method of detecting an analyte. The method includes: (a) contacting a sample including a cell with a polymeric separation medium including a microwell, where the polymeric separation medium includes functional groups that covalently bond one or more cellular components to the polymeric separation medium upon application of an applied stimulus; (b) contacting the polymeric separation medium with a buffer sufficient to differentially lyse a sub-cellular compartment of the cell to produce a set of cellular components; and (c) applying an electric field to the polymeric separation medium in a manner sufficient to move at least some of the set of cellular components into the polymeric separation medium to produce a set of separated cellular components in the polymeric separation medium.

In some embodiments, the contacting step (a) is sufficient to position the cell in the microwell.

In some embodiments, the contacting step (b) includes contacting a surface of the polymeric separation medium with a hydrogel layer that includes the buffer.

In some embodiments, the buffer is sufficient for the contacting step (b) and the applying step (c).

In some embodiments, the method includes immobilizing the set of separated cellular components in the polymeric separation medium. In some embodiments, the immobilizing includes covalently bonding the set of separated cellular components to the polymeric separation medium.

In some embodiments, the method further includes contacting the polymeric separation medium with a second buffer sufficient to differentially lyse a second sub-cellular compartment of the cell to produce a second set of cellular components.

In some embodiments, the method further includes applying an electric field to the polymeric separation medium in a manner sufficient to move at least some of the second set of cellular components into the polymeric separation medium to produce a second set of separated cellular components in the polymeric separation medium.

In some embodiments, the second set of cellular components is separated in a direction different from the first set of cellular components.

In some embodiments, the method includes immobilizing the second set of separated cellular components in the polymeric separation medium.

In some embodiments, the method includes detecting the separated cellular components.

In some embodiments, the detecting includes contacting the separated cellular components with an analyte detection reagent.

In some embodiments, the method includes contacting the separated cellular components with one or more secondary reagents.

In some embodiments, the method includes imaging the polymeric separation medium to produce an image of the separated cellular components.

Aspects of the present disclosure include a system for detecting an analyte. The system includes a polymeric separation medium that includes a microwell, where the polymeric separation medium includes functional groups that covalently bond one or more cellular components to the polymeric separation medium upon application of an applied stimulus. The system also includes a hydrogel layer that includes a buffer.

In some embodiments, the hydrogel layer is positioned on a surface of the polymeric separation medium such that the buffer is in fluid communication with the microwell.

In some embodiments, the microwell is dimensioned to accommodate a single cell.

In some embodiments, the polymeric separation medium includes an array of microwells in the polymeric separation medium.

In some embodiments, the polymeric separation medium includes 100 or more microwells.

Aspects of the present disclosure include a kit that includes a system according to the present disclosure, and a packaging containing the system.

In some embodiments, the kit includes one or more buffers.

BRIEF DESCRIPTION OF THE FIGURES

FIG. 3A shows a micrograph of fractionated U373 cells probed for GFP (cytosolic) and Lamin A/C (nuclear). Microwells are outlined with circles. FIG. 3B shows a conventional differential detergent fractionation in a bulk slab-gel Western blot that confirmed GFP and Lamin A/C localization, validating the microanalyses.

FIG. 4, panel B). FIG. 4, panel C shows a graph of a comparison of nonparametric parameters (mean+/−SD).

FIG. 5, panel A, shows histograms of nuclear NF-KappaB expression. FIG. 5, panel B, shows a scatter plot of median NF-KB localization during the translocation assay. FIG. 5, panel C, shows the Pearson correlation coefficient of the medians of ICC and subcellular Western blotting measurements during the translocation assay (rho=0.90).

DETAILED DESCRIPTION

Figure 1:
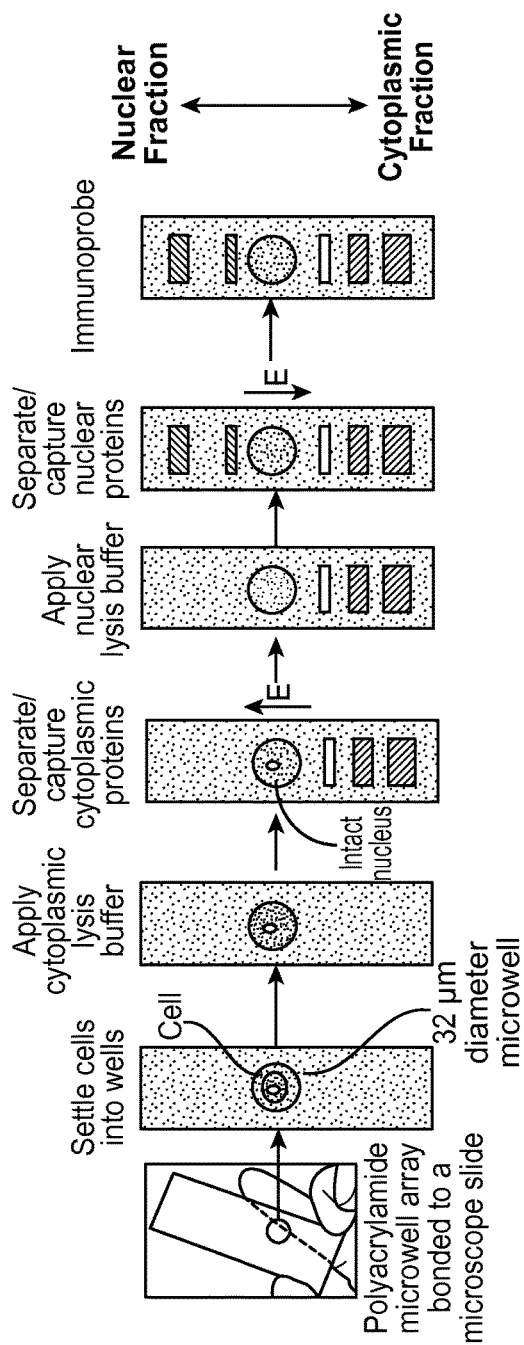
FIG. 1 shows a schematic of a sub-cellular single-cell Western blot according to embodiments of the present disclosure, which provided for cytosolic and nuclear protein measurements on the same single cell. A planar microarray format was used, which facilitated sub-cellular fraction analysis along distinct axes.

The present disclosure provides a method for performing Western blots on subcellular fractions of a cell. The Western blot analysis may be performed on subcellular fractions of a single cell. In some instances, the Western blot analysis is performed on subcellular fractions of the same single cell. In certain embodiments, an assay of the present disclosure enables the measurement of both protein localization and expression in a single cell. In certain embodiments, the fractionation of different subcellular compartments is achieved by the serial application of multifunctional buffers and multidirectional electrophoretic separations as described in the following sections of the present disclosure.

In addition to the methods described herein, electrophoretic separation devices and systems using the same are provided. For example, aspects of embodiments of the present disclosure include a device that includes a polymeric separation medium having a plurality of microwells. The polymeric separation medium includes functional groups that covalently bond to one or more sample components of interest in the separation medium upon application of an applied stimulus.

Below, the subject electrophoretic separation devices are described first in greater detail. Methods of detecting one or more analytes in a sample are also disclosed in which the subject devices find use. In addition, systems and kits that include the subject devices are also described.

Devices

Embodiments of the present disclosure include separation devices. In certain embodiments, the separation devices are configured to separate analytes in a sample.

For example, the separation devices may be configured to separate analytes in a sample based on one or more physical and/or chemical properties of the analytes. In some instances, the analytes may include detectable differences in their molecular weight, size, charge (e.g., mass to charge ratio), isoelectric point, affinity interactions, and the like. Separation devices of the present disclosure may be configured to distinguish different analytes from each other based on one or more of their molecular weight, size, charge (e.g., mass to charge ratio), isoelectric point, affinity interactions, and the like.

In certain embodiments, the separation devices are microfluidic separation devices. A "microfluidic device" is a device that is configured to control and manipulate fluids geometrically constrained to a small scale (e.g., sub-millimeter). Embodiments of the microfluidic devices include a polymeric medium, e.g., a polymeric separation medium as described in more detail herein. The polymeric medium may include a covalently bound capture member that specifically binds to an analyte of interest in a sample. The separation devices of the present disclosure may also be configured to perform assays on a larger scale, such as fluidic device configured to control and manipulate fluids on a millimeter (e.g., milliliter) scale, or larger.

In certain embodiments, the separation device includes a solid support. The solid support may be configured to support a polymeric medium (e.g., the polymeric separation medium). For example, the polymeric separation medium may be provided on the solid support, such that at least a portion of the polymeric separation medium is in contact with a surface of the solid support (e.g., the device includes a solid support carrying the polymeric medium). In some cases, the solid support is composed of a material that is inert (e.g., does not degrade or react) with respect to the samples, buffers, reagents, etc. used in the subject devices and methods. For instance, the solid support may be made of a material, such as, but not limited to, glass, quartz, polymers, elastomers, paper, combinations thereof, and the like. In certain embodiments, the solid support is substantially transparent. By "transparent" is meant that a substance allows visible light to pass through the substance. In some embodiments, a transparent solid support facilitates detection of analytes bound to the polymeric medium, for example analytes that include, produce, or are labeled with a detectable label, such as a fluorescent label. In some cases, the solid support is substantially opaque. By "opaque" is meant that a substance substantially blocks visible light from passing through the substance. In certain instances, an opaque solid support may facilitate the analysis of analytes that are sensitive to light, such as analytes that react or degrade in the presence of light.

In certain embodiments, the solid support is sized to accommodate the polymeric separation medium. For example the solid support may have dimensions (e.g., length and width) such that the entire polymeric separation medium is supported by the solid support. In some cases, the solid support may have dimensions (e.g., length and width) larger than the polymeric separation medium. In some instances, the solid support has dimensions in the range of 10 mm×10 mm to 200 mm×200 mm, including dimensions of 100 mm×100 mm or less, such as 50 mm×50 mm or less, for instance 25 mm×25 mm or less, or 10 mm×10 mm or less, or 5 mm×5 mm or less, for instance, 1 mm×1 mm or less.

In some cases, the solid support has a thickness ranging from 0.5 mm to 5 mm, or 1 mm to 4 mm, of 1 mm to 3 mm, or 1 mm to 2 mm. In certain instances, the solid support has a thickness of 1 mm.

As described above, the solid support may be configured to support a polymeric separation medium. Aspects of the polymeric separation medium are described in more detail below.

Polymeric Separation Medium

The polymeric separation medium may be configured to separate constituents of a sample from each other. In some cases, the separation medium is configured to separate constituents in a sample based on the physical properties of the constituents.

For example, the separation medium may be configured to separate the constituents in the sample based on the molecular mass, size, charge (e.g., charge to mass ratio), isoelectric point, affinity interactions, etc. of the constituents.

In certain instances, the separation medium is configured to separate the constituents in the sample based on the size and charge of the constituents. The separation medium may be configured to separate the constituents in the sample into distinct detectable bands of constituents. By "band" is meant a distinct detectable region where the concentration of a constituent is significantly higher than the surrounding regions. Each band of constituent may include a single constituent or several constituents, where each constituent in a single band of constituents has substantially similar physical properties, as described above.

In certain embodiments, the separation medium is configured to separate the constituents in a sample as the sample traverses the separation medium. In some cases, the separation medium is configured to separate the constituents in the sample as the sample flows through the separation medium. Aspects of the separation medium include that the separation medium has a directional separation axis, or in other cases a plurality of directional separation axes, as described in more detail below. In some instances, the directional separation axis is oriented in the direction the sample travels as the sample traverses the separation medium.

Polymeric Separation Medium with a Planar Array of Microwells

In certain embodiments, the polymeric separation medium includes a planar array of microwells. In these embodiments, the directional separation axis is aligned with the length (or the width) of the separation medium. For instance, the directional separation axis may be substantially parallel to the length (or the width) of the separation medium. In some embodiments, the separation medium is square or rectangular in shape and the directional axis of the separation medium may be aligned with the length (or width) of the separation medium. In these embodiments, the sample traverses the separation medium along its length (or width). In some cases, where the sample traverses the length of the separation medium, the length of the separation medium is greater than the width of the separation medium, such as 2 times, 3 times, 4 times, 5 times, 10 times, 25 times, 50 times, 75 times, 100 times, 125 times, 150 times, 175 times, or 200 times or more the width of the separation medium. In some instances, a longer separation axis may facilitate an increase in resolution between bands of different analytes in the sample.

In certain embodiments, the separation medium includes a plurality of microwells in the separation medium. In some instances, the separation medium includes a substantially planar array of microwells in the separation medium. An "array of microwells" includes any two-dimensional or substantially two-dimensional arrangement of microwells. For example, a planar array of microwells may be arranged into rows and columns of microwells. The microwells in the planar array of microwells may be individually addressable. A microwell is "addressable" when the array includes multiple microwells positioned at particular predetermined locations (e.g., "addresses") in the array. Microwells may be separated by intervening spaces. A planar array of microwells may include one or more, including two or more, four or more, eight or more, 10 or more, 25 or more, 50 or more, 100 or more, 200 or more, 300 or more, 400 or more, 500 or more, 750 or more, 1000 or more, 1500 or more, 2000 or more, 2500 or more, 3000 or more, 3500 or more, 4000 or more, 4500 or more, 5000 or more, 5500 or more, 6000 or more, 6500 or more, 7000 or more, 7500 or more, 8000 or more, 8500 or more, 9000 or more, 9500 or more, 10,000 or more, or 25,000 or more, or 50,000 or more, or 75,000 or more, or 100,000 or more microwells in a polymeric separation medium. In some cases, a planar array of microwells may include 5000 or more microwells. Each polymeric separation medium may include one or more arrays of microwells, for example, 1 or more, 2 or more, 3 or more, 4 or more, 5 or more, 6 or more, 7 or more, 8 or more, 9 or more, 10 or more, 12 or more, 14 or more, 16 or more, 18 or more, 20 or more, 25 or more, 30 or more, 35 or more, 40 or more, 45 or more, 50 or more, 75 or more, or 100 or more arrays or microwells. In some cases, the polymeric separation medium includes 10 or more arrays of microwells. Depending upon the use, any or all of the microwells may be the same or different from one another and each may be configured to contain distinct samples or sample constituents. Aspects of individual microwells are described in more detail below, but may be applied to any or all of the microwells in the array of microwells.

In certain embodiments, the polymeric separation medium includes a planar array of microwells as described above. The planar array of microwells may be arranged such that each microwell has an open end provided on a surface of the separation medium (e.g., on a top surface of the separation medium). In these embodiments, the interior volume of each microwell may extend from the open end of the microwell on the surface of the polymeric separation medium into the polymeric separation medium. In certain embodiments, the open end of the microwell (and thus the interior volume of the microwell) is in fluid communication with a fluid provided on the surface of the separation medium (e.g., buffer, sample, etc.). In some instances, the bottom (i.e., closed end) of the microwell is formed by the solid support supporting the polymeric separation medium, e.g., in embodiments where the interior volume of the microwell extends all the way through the separation medium, such as where the depth of the microwell equals the thickness of the polymeric separation medium. In other instances, the bottom (i.e., closed end) of the microwell is formed by the polymeric separation medium, e.g., in embodiments where the interior volume of the microwell does not extend all the way through the separation medium, such as where the depth of the microwell is less than the thickness of the polymeric separation medium.

In certain embodiments, the microwell is configured such that an axis of the microwell from the closed end to the open end of the microwell is substantially perpendicular to the surface of the separation medium (e.g., the surface of the separation medium having the open ends of the microwells). In certain embodiments, the walls (e.g., the side walls) of the microwell are formed by the polymeric separation medium, such as where the interior volume of the microwell extends into the polymeric separation medium and is surrounded by the polymeric separation medium.

Additional Aspects of Microwells

In certain embodiments, the microwell has an interior volume with a defined shape. For example, the interior volume of the microwell may have a shape of a cylinder, a cube, a rectangular cuboid, a frustum (e.g., a square frustum, a rectangular frustum, a conical frustum, etc.), and the like.

In certain embodiments, the open end of the microwell has dimensions greater than the closed end of the microwell. For instance, the open end of the microwell may have dimensions (e.g., width and/or length, or diameter, depending on the shape of the microwell) that are 1.1 times greater than the dimensions of the closed end of the microwell, such as 1.2 times, or 1.3 times, or 1.4 times, or 1.5 times, or 1.6 times, or 1.7 times, or 1.8 times, or 1.9 times, or 2 times the dimensions of the closed end of the microwell.

A "microwell" is a well that has dimensions in the micrometer scale. While the dimensions may vary, in some instances, the open end of the microwell has a width of 100 µm or less, such as 90 µm or less, or 80 µm or less, or 70 µm or less, or 60 µm or less, or 50 µm or less, or 40 µm or less, or 30 µm or less, or 20 µm or less, or 10 µm or less. For example, the open end of the microwell may have a width ranging from 10 µm to 100 µm, such as 10 µm to 90 µm, or 10 µm to 80 µm, or 10 µm to 70 µm, or 10 µm to 60 µm, or 10 µm to 50 µm, or 10 µm to 40 µm, or 10 µm to 30 µm. In certain embodiments, the microwell may have an open end dimensioned to accommodate a single cell in the microwell (e.g., a single cell in an individual microwell).

In some cases, the closed end of the microwell has a width of 100 µm or less, such as 90 µm or less, or 80 µm or less, or 70 µm or less, or 60 µm or less, or 50 µm or less, or 40 µm or less, or 30 µm or less, or 20 µm or less, or 10 µm or less. For example, the closed end of the microwell may have a width ranging from 10 µm to 100 µm, such as 10 µm to 90 µm, or 10 µm to 80 µm, or 10 µm to 70 µm, or 10 µm to 60 µm, or 10 µm to 50 µm, or 10 µm to 40 µm, or 10 µm to 30 µm, or 10 µm to 20 µm. In certain embodiments, the microwell may have a closed end dimensioned to accommodate a single cell in the microwell (e.g., a single cell in an individual microwell).

In certain embodiments, the microwell has a depth (e.g., the distance from the open end to the closed end of the microwell) of 100 µm or less, such as 90 µm or less, or 80 µm or less, or 70 µm or less, or 60 µm or less, or 50 µm or less, or 40 µm or less, or 30 µm or less, or 20 µm or less, or 10 µm or less. For example, the microwell may have a depth ranging from 10 µm to 100 µm, such as 10 µm to 90 µm, or 10 µm to 80 µm, or 10 µm to 70 µm, or 10 µm to 60 µm, or 20 µm to 60 µm, or 30 µm to 60 µm, or 40 µm to 60 µm. In certain embodiments, the microwell may have a depth dimensioned to accommodate a single cell in the microwell (e.g., a single cell in an individual microwell).

The microwells in the polymeric separation medium may be substantially uniform. For example, the shape and size of the microwells in the separation medium may be substantially uniform. In other embodiments, the microwells may be different, such as having a different shape, a different size, combinations thereof, and the like. A separation medium that includes different microwells may facilitate the analysis of different sample constituents at the same time. For instance, microwells that have different shapes and/or sizes may preferentially capture different shaped or sized sample components (e.g., different shaped or sized cells in the sample).

Additional Aspects of the Separation Medium

In certain embodiments, the separation medium includes a polymer, such as a polymeric gel. The polymeric gel may be a gel suitable for gel electrophoresis. The polymeric gel may include, but is not limited to, a polyacrylamide gel (e.g., methacrylamide gel), an agarose gel, and the like. The resolution of the separation medium may depend on various factors, such as, but not limited to, pore size, total polymer content (e.g., total acrylamide content), concentration of cross-linker, applied electric field, assay time, and the like. For instance, the resolution of the separation medium may depend on the pore size of the separation medium. In some cases, the pore size depends on the total polymer content of the separation medium and/or the concentration of cross-linker in the separation medium. In certain instances, the separation medium is configured to resolve analytes with molecular mass differences of 50,000 Da or less, or 25,000 Da or less, or 10,000 Da or less, such as 7,000 Da or less, including 5,000 Da or less, or 2,000 Da or less, or 1,000 Da or less, for example 500 Da or less, or 100 Da or less. In some cases, the separation medium may include a polyacrylamide gel that has a total acrylamide content, T (T=total concentration of acrylamide and bisacrylamide monomer, % w/v), ranging from 1% to 20%, such as from 3% to 15%, including from 5% to 10%. In some instances, the separation medium has a total acrylamide content of 7%. In certain cases, the separation medium has a total acrylamide content of 6%. In certain embodiments, the separation medium includes a polyacrylamide gel that has a crosslinker content, C (%w/v), ranging from 1% to 10%, such as from 2% to 7%, including from 2% to 5%. In some instances, the separation medium has a total crosslinker content of 3%.

In certain embodiments, the separation medium is configured to be formed from precursor moieties. For example, the separation medium may be a gel (e.g., a polyacrylamide gel) formed form gel precursors (e.g., polyacrylamide gel precursors, such as polyacrylamide gel monomers). The precursor moieties may be configured to react to form the separation medium. For instance, the gel precursors may be configured to react with each other to form the polyacrylamide gel separation medium. The reaction between the gel precursors may be activated by any suitable protocol, such as, but not limited to, chemical activation, light activation, etc. In some embodiments, the gel precursors are configured to be activated chemically, for example by contacting the gel precursors with an activation agent, such as, but not limited to, a peroxide. In some embodiments, the gel precursors are configured to be activated by light (i.e., photo-activated), for instance by contacting the gel precursors with light. The light may be of any wavelength suitable for activating the formation of the separation medium, and in some instances may have a wavelength associated with blue light in the visible spectrum. For example, the light used to activate formation of the separation medium may have a wavelength ranging from 400 nm to 500 nm, such as from 410 nm to 490 nm, including from 420 nm to 480 nm, or from 430 nm to 480 nm, or from 440 nm to 480 nm, or from 450 nm to 480 nm, or from 460 nm to 480 nm, or from 465 nm to 475 nm. In certain cases, the light used to activate formation of the separation medium has a wavelength ranging from 465 to 475 nm. In some instances, the light used to activate formation of the separation medium has a wavelength of 470 nm.

In some instances, the separation medium has dimensions in the range of 10 mm×10 mm to 200 mm×200 mm, including dimensions of 100 mm×100 mm or less, such as 50 mm×50 mm or less, for instance 25 mm×25 mm or less, or 10 mm×10 mm or less, or 5 mm×5 mm or less, for instance, 1 mm×1 mm or less. In some cases, the separation medium has a thickness ranging from 1 μm to 100 μm, such as from 10 μm to 75 μm, or from 10 μm to 50 μm, or from 20 μm to 50 μm. In some cases, the separation medium has a thickness of 30 μm. In certain embodiments, the separation medium includes a buffer. The buffer may be any convenient buffer used for gel electrophoresis. In certain embodiments, the buffer is a Tris buffer. In certain embodiments, the separation medium includes a buffer, such as a Tris-glycine buffer. For example, the buffer may include a mixture of Tris and glycine.

In certain embodiments, the buffer is sufficient to perform both lysis of cells or a portion thereof (e.g., differential lysis of a sub-cellular compartment) and electrophoresis of the cellular components released by lysis of the cell or portion thereof (e.g., differential lysis of a sub-cellular compartment). In some cases, the buffer is a buffer sufficient to differentially lyse a sub-cellular compartment of a cell to produce a set of cellular components. For instance, the buffer may be configured to lyse a first sub-cellular compartment, such as the cell membrane, without causing significant lysis of other sub-cellular compartments, such as the nuclear membrane. In some cases, the buffer is configured to selectively lyse the cell membrane such that cytosol is released from the cell without causing significant lysis of other sub-cellular compartments, such as the nuclear membrane. In certain embodiments, the buffer may be configured to lyse a different sub-cellular compartment, such as the nuclear membrane. In certain embodiments, the second buffer does not cause significant lysis of other sub-cellular compartments, such as mitochondria, plastids, or other organelles. In some cases, the second buffer is configured to selectively lyse the nuclear membrane such that the contents of the cell nucleus are released from the nucleus without causing significant lysis of other sub-cellular compartments, such as mitochondria, plastids, or other organelles. Different buffers may be used sequentially in different steps of the methods described herein in achieve differential lysis of sub-cellular compartments of the cell, such that the contents of different sub-cellular compartments of a cell may be analyzed in series. In some embodiments, the buffer may be heated to a temperature above room temperature. For instance, the buffer may be heated to a temperature of 25° C. or more, or 30° C. or more, or 35° C. or more, or 40° C. or more, or 45° C. or more, or 50° C. or more, or 55° C. or more, or 60° C. or more, or 65° C. or more, or 70° C. or more, or 75° C. or more. In some cases, the buffer is heated to 50° C.

In some cases, the buffer includes a detergent. In certain instances, the detergent is configured to provide analytes in the sample with substantially similar charge-to-mass ratios. Analytes with substantially similar charge-to-mass ratios may facilitate the separation of the analytes into one or more bands in the separation medium based on the molecular masses of the analytes in the sample. In certain cases, the detergent is anionic detergent configured to provide analytes in the sample with a charge, such as a negative charge. For example, the detergent may be an anionic detergent, such as, but not limited to, sodium dodecyl sulfate (SDS). In some instances, the detergent may be digitonin. In some instances, the detergent may be sodium deoxycholate. Combinations of detergents may also be included in the buffer.

In certain embodiments, the buffer is configured to selectively lyse the cell membrane such that cytosol is released from the cell without causing significant lysis of other sub-cellular compartments, such as the nuclear membrane; e.g., the buffer is a cytosol lysis buffer. Examples of cytosol lysis buffers include, but are not limited to, Triton X-100, Tris-glycine, combinations thereof, and the like. In some instances, the cytosol lysis buffer may include a detergent, such as, but not limited to digitonin. For example, a cytosol lysis buffer may include Triton X-100, Tris-glycine and digitonin.

In certain embodiments, the buffer is configured to selectively lyse the nuclear membrane such that the contents of the cell nucleus are released from the nucleus without causing significant lysis of other sub-cellular compartments, such as mitochondria, plastids, or other organelles; e.g., the buffer is a nuclear lysis buffer. Examples of nuclear lysis buffers include, but are not limited to, Triton X-100, Tris-glycine, combinations thereof, and the like. In some instances, the nuclear lysis buffer may include a detergent, such as, but not limited to SDS, sodium deoxycholate, combinations thereof, and the like. For example, a nuclear lysis buffer may include Triton X-100, Tris-glycine, SDS, and sodium deoxycholate.

In certain embodiments, the separation medium is configured to separate the constituents in the sample based on the isoelectric point (p1) of the constituents (e.g., isoelectric focusing, IEF). In some cases, the separation medium includes a polymeric gel as described above. For example, the polymeric gel may include a polyacrylamide gel, an agarose gel, and the like. In certain instances, the polymeric gel includes a pH gradient, which, in some embodiments, is co-polymerized with the polymeric gel. In embodiments where the pH gradient is co-polymerized with the polymeric gel, the pH gradient may be substantially immobilized resulting in a separation medium having an immobilized pH gradient. In certain instances, the pH gradient includes a weak acid or a weak base (e.g., Immobilines), ampholytes, or the like.

In certain embodiments, the separation medium is configured to separate constituents in a sample based on size. For example, in some cases, the separation medium includes a polymeric gel having a pore size gradient. The pore size gradient may decrease along the directional axis of the separation medium. For example, the pore size gradient may have a pore size that decreases along the directional axis of the separation medium, such that a sample traversing the separation medium encounters progressively smaller and smaller pore sizes in the separation medium. As constituents in the sample traverse the pore size gradient, the constituents in the sample may be separated based on size. For example, larger constituents in the sample may be retained in the separation medium more readily than smaller constituents, which are able to traverse greater distances through the decreasing pore size gradient.

In some cases, the pore size of the separation medium depends on the total polymer content of the separation medium and/or the concentration of crosslinker in the separation medium. In certain instances, the separation medium pore size sufficient to resolve analytes with molecular mass differences of 50,000 Da or less, or 25,000 Da or less, or 10,000 Da or less, such as 7,000 Da or less, including 5,000 Da or less, or 2,000 Da or less, or 1,000 Da or less, for example 500 Da or less, or 100 Da or less. In some cases, the separation medium may include a polyacrylamide gel that has a pore size that depends on the total acrylamide content, T (T=total concentration of acrylamide and bisacrylamide monomer), where the total acrylamide content, T, ranges from 1% to 20%, such as from 3% to 15%, including from 5% to 10%. In some instances, the separation medium has pore size defined by a total acrylamide content of 7%. In certain cases, the separation medium has a pore size defined by a total acrylamide content of 6%. In certain embodiments, the separation medium includes a polyacrylamide gel that has a crosslinker content, C (%w/v), ranging from 1% to 10%, such as from 2% to 7%, including from 2% to 5%. In some instances, the separation medium has a total crosslinker content of 3%.

In certain embodiments, the separation medium is configured to covalently bond to the constituents of interest. The covalent bond may be formed upon application of an applied stimulus. For example, the applied stimulus may include electromagnetic radiation, such as light. In some cases, the light is ultraviolet (UV) light. In some instances, the light used to covalently bond the constituents of interest to the separation medium has a wavelength ranging from 10 nm to 400 nm, such as from 50 nm to 400 nm, including from 100 nm to 400 nm, or from 150 nm to 400 nm, or from 200 nm to 400 nm, or from 250 nm to 400 nm, or from 300 nm to 400 nm, or form 325 nm to 375 nm, or from 350 nm to 365 nm. In certain cases, the light has a wavelength ranging from 350 to 365 nm.

In certain embodiments, the light used to covalently bond the constituents of interest to the separation medium has a wavelength different from the light used to activate formation of the separation medium. For example, as described above, the light used to activate formation of the separation medium may have a wavelength of blue light in the visible spectrum. As described above, the light used to covalently bond the constituents of interest to the separation medium may have a wavelength of UV light. As such, in certain embodiments, the separation medium is configured to be formed upon application of a first wavelength of light, and configured to covalently bond the constituents of interest upon application of a second wavelength of light. The first and second wavelengths of light may be blue light and UV light, respectively, as described above.

In some cases, the separation medium includes functional groups that covalently bond to the one or more constituents of interest. For example, the constituents of interest may be an analyte of interest, such as, but not limited to, a protein, a peptide, and the like. The functional groups may include functional groups that are activated upon application of an applied stimulus, such as electromagnetic radiation (e.g., light) as described above. As such, in certain instances, the functional groups are light-activatable functional groups. Upon application of light, the light-activatable functional groups may form a reactive species capable of forming covalent bonds, such as a radical alkyl intermediate. Examples of functional groups that may covalently bond to the constituents of interest upon application of an applied stimulus (e.g., light) include, but are not limited to, benzophenone groups, and the like. Once activated by the applied stimulus, the functional group may bond to the constituent of interest (e.g., protein or peptide) forming a covalent bond between the separation medium and the constituent of interest. For example, the functional group may form a carbon-carbon bond between the functional group and the constituent of interest.

In some embodiments, the functional groups are co-polymerized with the separation medium. For example, the functional groups may include a linker group that is attached to the separation medium. The functional group may be bound to the linker group at a first end of the linker group, and a second end of the linker group may be bound to the separation medium, thereby indirectly bonding the functional group to the separation medium. In some instances, the second end of the linker group, which is bound to the separation medium, includes a co-monomer, such as, but not limited to, an acrylamide co-monomer, and the like. In some embodiments, the second end of the linker group includes a methacrylamide co-monomer. In certain cases, the functional group is a benzophenone functional group and the linker group includes a co-monomer, such as an acrylamide co-monomer. For example, the functional group (including the linker group) may be N-(3-[(4-benzoylphenyl)formamido]propyl) methacrylamide (also known as BPMA or BPMAC) or 3-benzoyl-N-[3-(2-methyl-acryloylamino)-propyl]-benzamide (BP-APMA); the structures of each of which are shown below. As described above, the linker group may have the functional group attached at a first end, and the second end of the linker group bound to the polymeric medium. In some instances, the linker group includes a spacer group, such as a spacer group between the first end and the second end of the linker group (e.g., a spacer group in the middle portion of the linker group between the functional group and the co-monomer). In some cases, the spacer group of the linker group between the first and second ends of the linker group includes an aliphatic group, such as, but not limited to, a $C_{1-10}$ alkyl group. In certain cases, the spacer group of the linker group includes a lower alkyl group (e.g., a $C_{1-6}$ alkyl group, or a $C_{1-5}$ alkyl group, or a $C_{1-4}$ alkyl group, or a $C_{1-3}$ alkyl group, or a $C_{1-2}$ alkyl group). For instance, the spacer group of the linker group may include a propyl group.

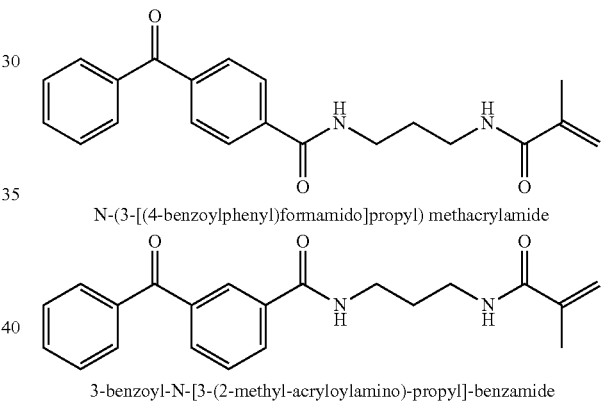

N-(3-[(4-benzoylphenyl)formamido]propyl) methacrylamide 3-benzoyl-N-[3-(2-methyl-acryloylamino)-propyl]-benzamide An embodiment of the functional groups that may be co-polymerized with the separation medium is a cross-linked polyacrylamide gel separation medium that includes photoactive benzophenone functional groups. The photoactive benzophenone groups may be activated by light to form covalent bonds to constituents of interest (e.g., proteins in the separated sample).

In certain embodiments, the separation medium is configured to bind to constituents in a sample at a minimum capture efficiency. The capture efficiency is the percentage of constituents in the sample that are bound by the separation medium. In some instances, the capture efficiency, $\eta$, is the ratio of fluorescence measured after gradient washout ($AFU_w$) to the fluorescence during focusing ($AFU_f$), corrected by a factor E to account for the anticipated influence of pH on the species fluorescence signal. In certain embodiments, the separation medium is configured to have a capture efficiency of 1% or more, such as 5% or more, including 10% or more, or 20% or more, or 30% or more, or 40% or more, or 50% or more, or 60% or more, or 70% or more, or 80% or more, or 90% or more, or 95% or more. In some instances, the separation medium has a capture efficiency of 75% or more.

Additional aspects of the polymeric separation medium are described in U.S. Application Publication No. 2011/0177618, filed May 18, 2010, U.S. Application Publication No. 2012/0329040, filed Jun. 21, 2012, and PCT/US2014/021399, filed Mar. 6, 2014, the disclosures of each of which are incorporated herein by reference.

Methods

Embodiments of the methods are directed to separating constituents of a sample, such as constituents of a cell (e.g., cellular components). Aspects of the method include contacting a sample, such as a sample that includes a cell, with a polymeric separation medium that includes a microwell as described above. The polymeric separation medium includes functional groups that covalently bond one or more cellular components of interest to the separation medium upon application of an applied stimulus, as described in more detail below. Additional aspects of the method include contacting the polymeric separation medium with a buffer sufficient to differentially lyse a sub-cellular compartment of the cell to produce a set of cellular components. The method also include applying an electric field to the polymeric separation medium in a manner sufficient to move at least some of the set of cellular components into the polymeric separation medium to produce a set of separated cellular components in the polymeric separation medium. These and other aspects of the methods according to embodiments of the present disclosure are described in the following sections.

As described above, methods of the present disclosure include contacting a sample that includes a cell to a polymeric separation medium that includes a microwell. In certain embodiments, the sample may be contacted to the polymeric separation medium such that constituents of the sample (e.g., cells) are positioned in one or more microwells in the polymeric separation medium. For example, the sample may be applied to a surface of the separation medium and the constituents in the sample may be allowed to passively settle into the microwells, e.g., passively settle out of solution due to gravity). In some instances, as described above, the polymeric separation medium includes a planar array of microwells, and in some cases the sample constituents may be positioned in the planar array of microwells by applying the sample to the separation medium and allowing the constituents in the sample to passively settle into the planar array of microwells. In certain embodiments, the array of microwells may include microwells that have substantially uniform, or in other embodiments non-uniform, shapes and/or sizes as described above. In embodiments, where the polymeric separation medium includes non-uniform microwells, the method may include size selected settling using different shaped and/or sized microwells. For example, a sample may be applied to the separation medium and sample constituents (e.g., cells) may preferentially settle into certain corresponding microwells depending on the shape and/or size of the cells and microwells.

As described above, in certain embodiments a microwell of the polymeric separation medium is dimensioned to accommodate a single cell in the microwell, e.g., an individual microwell is dimensioned to accommodate a single cell. As such, embodiments of methods of the present disclosure may include contacting a sample that includes a cell (or a plurality of cells) to a microwell such that an individual microwell contains a single cell. In some embodiments, each microwell of the polymeric separation medium is dimensioned such that a single cell will fit in each individual microwell. Thus, a sample containing a plurality of cells may be contacted to a polymeric separation medium that includes an array of a plurality of microwells, such that individual microwells of the polymeric separation medium may contain a single cell from the sample. Depending on factors, such as how fast the cells passively settle into the mirowells, one or more individual microwells of the polymeric separation medium may contain a single cell.

As described above, the method includes contacting the polymeric separation medium with a buffer sufficient to differentially lyse a sub-cellular compartment of the cell to produce a set of cellular components. By "differentially lyse" or "differential lysis" is meant that the buffer is capable of selectively lysing a specific sub-cellular compartment of the cell without causing significant lysis of other sub-cellular compartment(s) of the cell. For instance, a buffer may be configured to lyse a first sub-cellular compartment, such as the cell membrane, without causing significant lysis of other sub-cellular compartments, such as the nuclear membrane. In some cases, the buffer is configured to selectively lyse the cell membrane such that cytosol is released from the cell without causing significant lysis of other sub-cellular compartments, such as the nuclear membrane. The released cellular components (e.g., cytosol and cellular components contained therein) of the first sub-cellular compartment may then be analyzed (e.g., separated) in the polymeric separation medium. For example, as described herein, the method may include applying an electric field to the polymeric separation medium in a manner sufficient to move at least some of the first set of cellular components (e.g., cytosol components) into the polymeric separation medium to produce a first set of separated cellular components (e.g., a set of separated cytosol components) in the polymeric separation medium. In certain embodiments, the same is buffer sufficient for differentially lysing a sub-cellular compartment and for performing the separation in the polymeric separation medium. Stated another way, the same buffer may be used to lyse the first sub-cellular compartment and also may be used for the electrophoretic separation of the first set of cellular components (e.g., cytosol components) in the polymeric separation medium.

In certain embodiments, the method includes contacting the polymeric separation medium with a second buffer sufficient to differentially lyse a second sub-cellular compartment of the cell to produce a second set of cellular components. For instance, a second buffer may be configured to lyse a second sub-cellular compartment, such as the nuclear membrane. In certain embodiments, the second buffer does not cause significant lysis of other sub-cellular compartments, such as mitochondria, plastids, or other organelles. In some cases, the second buffer is configured to selectively lyse the nuclear membrane such that the contents of the cell nucleus are released from the nucleus without causing significant lysis of other sub-cellular compartments, such as mitochondria, plastids, or other organelles. The released cellular components of the second sub-cellular compartment (e.g., nucleus) may then by analyzed (e.g., separated) in the polymeric separation medium. For example, as described herein, the method may include applying an electric field to the polymeric separation medium in a manner sufficient to move at least some of the second set of cellular components (e.g., nuclear components) into the polymeric separation medium to produce a second set of separated cellular components (e.g., a set of separated nuclear components) in the polymeric separation medium. In certain embodiments, the same is buffer sufficient for differentially lysing a sub-cellular compartment and for performing the separation in the polymeric separation medium. Stated another way, the same buffer may be used to lyse the second sub-cellular compartment and may also be used for the electrophoretic separation of the second set of cellular components (e.g., nuclear components) in the polymeric separation medium. In certain cases, the second buffer is different from the first buffer described above.

In certain instances, the separation of the first set of sub-cellular components is performed in a first direction in the polymeric separation medium. In some cases, the separation of the second set of sub-cellular components if performed in a second direction in the polymeric separation medium. The first direction and the second direction may be different directions in the polymeric separation medium. For instance, the first direction and second direction may be along separation axes in opposite directions (e.g., 180 degrees apart). In other instances, the first direction and second direction may be along separation axes that are 90 degrees apart. In some instances, the first direction and second direction are both coplanar with the plane of the polymeric separation medium, such that separation of the first and second set of sub-cellular components occurs within the plane of the polymeric separation medium.

In certain embodiments, the method includes further lysis of additional sub-cellular compartments in series, such that cellular components of the additional sub-cellular compartments may be analyzed (e.g., separated) in series. The other sub-cellular compartments that may be differentially lysed and analyzed using the methods and systems of the present disclosure may include, but are not limited to mitochondria, plastids, and other organelles. In certain embodiments, each set of cellular components is separated in the polymeric separation medium in a different direction in the polymeric separation medium.

In certain embodiments, contacting the polymeric separation medium with a buffer includes contacting a surface of the polymeric separation medium with a composition that includes the buffer. The buffer composition may be a composition configured to act as a carrier for the buffer. For example, the buffer composition may be a hydrogel that includes the buffer. The buffer composition may be applied as a layer on the surface of the polymeric separation medium. As such, in some instances, the method includes contacting a surface of the polymeric separation medium (e.g., a top surface) with a hydrogel layer that includes the buffer. The buffer composition may be applied to the surface of the polymeric separation medium after contacting the polymeric separation medium with the sample (and after a cell from the sample becomes positioned in a microwell). In some embodiments, the buffer composition is applied to the surface of the polymeric separation medium such that substantially the entire surface of the polymeric separation medium in in contact with the buffer composition. The buffer composition may be in fluidic communication with the surface of the polymeric separation medium. For instance, the buffer composition may be in fluidic communication with the surface of the polymeric separation medium such that buffer from the buffer composition may diffuse from the buffer composition into the polymeric separation medium and/or into the microwells of the polymeric separation medium. As described above, the buffer may differentially lyse a sub-cellular compartment of a cell in the microwell to produce a set of cellular components that may be analyzed (e.g., separated) in the polymeric separation medium.

In other embodiments, as described above, the polymeric separation medium may include a circular arrangement of microwells. In these embodiments, the method of positioning the sample constituents in the microwells may include applying a centrifugal force to the polymeric separation medium in a manner sufficient to position components of the sample in the microwells. For example, the sample may be introduced into the central well of the polymeric separation medium, and then a centrifugal force may be applied (e.g., by spinning the device) such that sample constituents (e.g., cells) in the central well are forced into one or more microwells on the periphery of the central well. As described herein, each individual microwell in the polymeric separation medium may be dimensioned to accommodate a single cell. Stated another way, an individual microwell may have dimensions such that only a single call is contained in the microwell.

In some instances, the applied centrifugal force may be of a magnitude sufficient to position a sample component, such as a cell, into a microwell of the device. In certain instances, the applied centrifugal force may be of a magnitude sufficient to position a sample component, e.g., a cell, into a microwell of the device without causing significant damage to the constituents in the sample (e.g., cells). In certain instances, the applied centrifugal force is 50 g (gravitational force) or more, such as 60 g or more, or 70 g or more, or 80 g or more, or 90 g or more, or 100 g or more, or 110 g or more, or 120 g or more, or 130 g or more, or 140 g or more, or 150 g or more.

Other methods of positioning sample constituents into a microwell are also possible. For example, sample constituents may be positioned in one or more microwells of the polymeric separation medium by one or more or the following: applying an electric field to the sample; applying a density gradient, physically positioning the sample constituents into the microwell using a positioning device, such as but not limited to a micropipetter, a nozzle, optical tweezers, and the like; applying a pressure force; applying a magnetic force (e.g., where the sample constituents of interest are bound to magnetic beads); convection flow; size selected settling using different sized microwells; positioning droplets of sample containing cells or cell lysates into microwells; combinations thereof, and the like.

In certain embodiments, the sample and/or sample components may be manipulated prior to or after positioning the sample components into the microwells. For example, the sample and/or sample components may be manipulated prior to positioning into the microwells. In other embodiments, the sample and/or sample components may be manipulated after positioning into the microwells. In some instances, the sample may include one or more cells of interest. As such, the method may include manipulating the cell to produce cellular components. For instance, the method may include lysing the cell to release cellular components from the cell. In some instances, the cellular components may be produced by differential lysis of specific cellular compartments. For example, differential lysis of specific cellular compartments may facilitate the individual analysis of the contents of different cellular compartments. In certain cases, the cellular components may be produced from the cell by treating the cell such that the cell releases the cellular component of interest (e.g., without lysing the cell). For example, the cell may be treated (e.g., incubated in a warmer or cooler temperature, treated with an active agent, etc.) such that the cell secretes one or more cellular components of interest. In certain embodiments, the cell may be encapsulated in a sample droplet and the sample droplet may be treated as described above such that cellular components are produced. The droplets may be positioned in the microwells and then treated as described above, or the droplets may be treated prior to positioning the droplets in the microwells.

Once the sample constituents are positioned in the microwells, the method may further include separating the sample constituents in the separation medium to produce separated sample constituents. In some cases, the separated constituents are produced by gel electrophoresis as the sample traverses from the microwell through a wall of the microwell and through the separation medium. In other cases, the separated sample is produced by isoelectric focusing in the separation medium. The separated sample may include distinct detectable bands of constituents (e.g., analytes), where each band includes one or more constituents that have substantially similar properties, such as molecular mass, size, charge (e.g., charge to mass ratio), isoelectric point, affinity interaction, etc. depending on the type of separation performed.

For example, in embodiments where the polymeric separation medium includes a planar array of microwells as described herein, the method may include separating the sample constituents by applying an electric field across the polymeric separation medium in a manner sufficient to move at least some of the sample constituents through a side wall of the microwell and into the polymeric separation medium to produce separated sample constituents in the polymeric separation medium as the sample constituents traverse through the separation medium. In other embodiments where the polymeric separation medium includes a circular arrangement of microwells as described above, the method may include separating the sample constituents by applying an electric field across the polymeric separation medium in a manner sufficient to move at least some of the sample constituents through the closed end of the microwell (e.g., the bottom of the microwell) and into the polymeric separation medium to produce separated sample constituents in the polymeric separation medium as the sample constituents traverse through the separation medium.

In certain embodiments, the device is configured to subject a sample to an electric field. The electric field may facilitate the movement of the sample through the device (e.g., electrokinetic transfer of the sample from one region of the device to another region of the device). The electric field may also facilitate the separation of the analytes in the sample by electrophoresis (e.g., polyacrylamide gel electrophoresis (PAGE), SDS-PAGE, isoelectric focusing, etc.), as described above.

For instance, separating the analytes in a sample may include applying an electric field configured to direct the analytes in the sample through the separation medium of the device. The electric field may be configured to facilitate the separation of the analytes in a sample based on the physical properties of the analytes. For example, the electric field may be configured to facilitate the separation of the analytes in the sample based on the molecular mass, size, charge (e.g., charge to mass ratio), isoelectric point, etc. of the analytes. In certain instances, the electric field is configured to facilitate the separation of the analytes in the sample based on the molecular mass of the analytes. In other embodiments, the electric field is configured to facilitate separation of the analytes in the sample based on the isoelectric point (p1) of the analytes.

In some instances, the methods further include immobilizing the separated sample components in the polymeric separation medium. Immobilizing may be accomplished using any convenient approach, e.g., covalently bonding the separated sample components to the polymeric separation medium, such as by exposing the polymeric separation medium to ultra-violet (UV) light. For example, after the constituents in the sample have been separated, the method may further include applying a stimulus to the separation medium to covalently bond the constituents to the separation medium. In some cases, the applying the stimulus includes applying electromagnetic radiation to the separation medium. For instance, the method may include exposing the separation medium to light, such as, but not limited to, visible light, UV light, infrared light, etc. In certain cases, the method includes applying light (e.g., UV light) to the separation medium to covalently bond the constituents to the separation medium.

As such, in certain embodiments, the method includes immobilizing the set of separated cellular components in the polymeric separation medium as described above. The set of separated cellular components may be the set of cellular components produced by differential lysis of a sub-cellular compartment (e.g., cytosol) as described above. In some instances, following immobilization of a first set of cellular components in the polymeric separation medium, the polymeric separation medium is contacted with a second buffer sufficient to differentially lyse a second sub-cellular compartment of the cell to produce a second set of cellular components, as described above. The second set of cellular components may be analyzed (e.g., separated) in the polymeric separation medium as described above. In some cases, the method further includes immobilizing the second set of separated cellular components in the polymeric separation medium. The second set of separated cellular components may be the set of cellular components produced by differential lysis of a sub-cellular compartment (e.g., nucleus) as described above.

In certain embodiments, the light used to covalently bond the constituents of interest to the separation medium has a wavelength different from the light used to activate formation of the separation medium. For example, as described herein, the light used to activate formation of the separation medium may have a wavelength of blue light in the visible spectrum. As described above, the light used to covalently bond the constituents of interest to the separation medium may have a wavelength of UV light. As such, in certain embodiments, the method includes exposing the separation medium to a first wavelength of light to form the separation medium, and exposing the separation medium to a second wavelength of light to covalently bond the constituents of interest to the separation medium. The first and second wavelengths of light may be blue light and UV light, respectively, as described herein.

In certain embodiments, the method includes determining whether an analyte of interest is present in a sample, e.g., determining the presence or absence of one or more analytes of interest in a sample. In some instances, the devices are configured to detect the presence of one or more analytes in a sample. In certain embodiments of the methods, the presence of one or more analytes in the sample may be determined qualitatively or quantitatively. Qualitative determination includes determinations in which a simple yes/no result with respect to the presence of an analyte in the sample is provided to a user. Quantitative determination includes both semi-quantitative determinations in which a rough scale result, e.g., low, medium, high, is provided to a user regarding the amount of analyte in the sample and fine scale results in which a measurement of the concentration of the analyte is provided to the user.

In certain embodiments, the method includes detecting an analyte of interest bound to the separation medium. Detectable binding of an analyte of interest to the separation medium indicates the presence of the analyte of interest in the sample. In some instances, detecting the analyte of interest includes contacting the analyte of interest with a label configured to specifically bind to the analyte of interest, e.g., as may be present in an analyte detection reagent. The analyte detection reagent can be any molecule that specifically binds to a protein or nucleic acid sequence or biomacromolecule that is being targeted (e.g., the analyte of interest). Depending on the nature of the analyte, the analyte detection reagent can be, but is not limited to: single strands of DNA complementary to a unique region of the target DNA or RNA sequence for the detection of nucleic acids; antibodies against an epitope of a peptidic analyte for the detection of proteins and peptides; or any recognition molecule, such as a member of a specific binding pair. For example, suitable specific binding pairs include, but are not limited to: a member of a receptor/ligand pair; a ligand-binding portion of a receptor; a member of an antibody/antigen pair; an antigen-binding fragment of an antibody; a hapten; a member of a lectin/carbohydrate pair; a member of an enzyme/substrate pair; biotin/avidin; biotin/streptavidin; digoxin/antidigoxin; a member of a DNA or RNA aptamer binding pair; a member of a peptide aptamer binding pair; and the like. In certain embodiments, the analyte detection reagent includes an antibody. The antibody may specifically bind to the analyte of interest.

In certain embodiments, the analyte detection reagent includes a detectable label. Detectable labels include any convenient label that may be detected using the methods and systems, and may include, but are not limited to, fluorescent labels, colorimetric labels, chemiluminescent labels, multicolor reagents, enzyme-linked reagents, avidin-streptavidin associated detection reagents, radiolabels, gold particles, magnetic labels, and the like. In certain embodiments, the analyte detection reagent includes an antibody associated with a detectable label. For example, the analyte detection reagent may include a labeled antibody (e.g., a fluorescently labeled antibody) that specifically binds to the analyte of interest. As such, the method may include detecting the labeled analyte of interest.

As described above, detecting the analyte of interest includes contacting the analyte of interest with an analyte detection reagent (e.g., a label) configured to specifically bind to the analyte of interest (e.g., an antibody that specifically binds to the analyte of interest). For example, contacting the analyte of interest with an analyte detection reagent may include applying a solution of analyte detection reagent to the polymeric separation medium. The analyte detection reagent may be contacted to any surface of the polymeric separation medium, such as the top or one or more sides of the polymeric separation medium. In some cases, the analyte detection reagent may be moved through the polymeric separation medium such that the analyte detection reagent contacts analytes of interest immobilized within the polymeric separation medium. For instance, the analyte detection reagent may be moved through the polymeric separation medium by applying an electric field to the polymeric separation medium, applying a pressure, applying a centrifugal force, passive diffusion, and the like.

In certain embodiments, detecting the analyte of interest includes contacting the analyte of interest with a primary label that specifically binds to the analyte of interest. In certain embodiments, the method includes enhancing the detectable signal from the labeled analyte of interest. For instance, enhancing the detectable signal from the labeled analyte of interest may include contacting the primary label with a secondary label configured to specifically bind to the primary label. In certain instances, the primary label is a primary antibody that specifically binds to the analyte of interest, and the secondary label is a secondary antibody that specifically binds to the primary antibody. As such, enhancing the detectable signal from the labeled analyte of interest may include contacting the primary antibody with a secondary antibody configured to specifically bind to the primary antibody. The use of two or more detectable labels as described above may facilitate the detection of the analyte of interest by improving the signal-to-noise ratio.

In certain embodiments, the analyte detection reagent may not specifically bind to an analyte of interest. In some cases, the analyte detection reagent may be configured to produce a detectable signal from the analyte of interest without specifically binding to the analyte of interest. For example, the analyte of interest may be an enzyme (e.g., a cellular enzyme) and the analyte detection reagent may be a substrate for the enzyme. In some cases, contacting the analyte detection reagent (e.g., enzyme substrate) to the analyte of interest (e.g., enzyme) may produce a detectable signal as the substrate is converted by the enzyme.

In certain embodiments, the method includes removing the analyte detection reagent and then contacting the analyte of interest with another analyte detection reagent (e.g., stripping and reprobing). For instance, the method may include contacting the labeled analyte of interest with a buffer (e.g., a stripping buffer) configured to dissociate the analyte detection reagent from the analyte of interest. The dissociated analyte detection reagent may then be washed from the polymeric separation medium. In some cases, the analyte of interest may then be contacted with a subsequent analyte detection reagent. The subsequent analyte detection reagent may be the same or different from the initial analyte detection reagent. Stripping and reprobing may facilitate contacting analytes of interest with different analyte detection reagents.

In certain embodiments, detecting the analyte of interest includes imaging the polymeric separation medium to produce an image of the separated cellular components. Imaging the polymeric separation medium may be performed using any convenient imaging device, such as, but not limited to, a camera, a UV detector, a fluorescent detector, combinations thereof, and the like.

In certain embodiments, the method includes storing the polymeric separation medium. For example, the method may include storing the polymeric separation medium by dehydrating the polymeric separation medium. The polymeric separation medium may be stored for an extended period of time, such as, but not limited to, 1 day, 2 days, 3 days, 4 days, 5 days, 6 days, 1 week, 2 weeks, 3 weeks, 1 month, 2 months, 3 months, 4 months, 5 months, 6 months or more. In some embodiments, the method further includes rehydrating the polymeric separation medium. The rehydrated polymeric separation medium may be used in any of the assay steps described herein. For example, dehydrating and rehydrating the polymeric separation medium may be performed between any of the assay steps, such as, between producing the polymeric separation medium and performing an assay, between immobilizing the analytes of interest to the polymeric separation medium and contacting the analytes with an analyte detection reagent, between stripping and reprobing, etc.

Samples that may be assayed with the subject methods may include both simple and complex samples. Simple samples are samples that include the analyte of interest, and may or may not include one or more molecular entities that are not of interest, where the number of these non-interest molecular entities may be low, e.g., 10 or less, 5 or less, etc. Simple samples may include initial biological or other samples that have been processed in some manner, e.g., to remove potentially interfering molecular entities from the sample. By "complex sample" is meant a sample that may or may not have the analyte of interest, but also includes many different proteins and other molecules that are not of interest. In some instances, the complex sample assayed in the subject methods is one that includes 10 or more, such as 20 or more, including 100 or more, e.g., $10^3$ or more, $10^4$ or more (such as 15,000; 20,000 or 25,000 or more) distinct (i.e., different) molecular entities, that differ from each other in terms of molecular structure or physical properties (e.g., molecular mass, size, charge, isoelectric point, affinity interaction, etc.).

In certain embodiments, the analyte of interest are cells and/or cellular components. In some cases, the cells are obtained from samples (e.g., biological samples), such as, but not limited to, urine, blood, serum, plasma, saliva, semen, prostatic fluid, nipple aspirate fluid, lachrymal fluid, perspiration, feces, cheek swabs, cerebrospinal fluid, cell lysate samples, amniotic fluid, gastrointestinal fluid, biopsy tissue (e.g., samples obtained from laser capture microdissection (LCM)), and the like. The sample can be a biological sample or can be extracted from a biological sample derived from humans, animals, plants, fungi, yeast, bacteria, tissue cultures, viral cultures, or combinations thereof using conventional methods for the successful extraction of DNA, RNA, proteins and peptides. In certain embodiments, the sample is a fluid sample, such as a solution of analytes (e.g., cells and/or cellular components) in a fluid. The fluid may be an aqueous fluid, such as, but not limited to water, a buffer, and the like.

As described above, the samples that may be assayed in the subject methods may include one or more analytes of interest. Examples of detectable analytes include, but are not limited to: nucleic acids, e.g., double or single-stranded DNA, double or single-stranded RNA, DNA-RNA hybrids, DNA aptamers, RNA aptamers, etc.; proteins and peptides, with or without modifications, e.g., antibodies, diabodies, Fab fragments, DNA or RNA binding proteins, phosphorylated proteins (phosphoproteomics), peptide aptamers, epitopes, and the like; small molecules such as inhibitors, activators, ligands, etc.; oligo or polysaccharides; mixtures thereof; and the like.

In certain embodiments, the method is configured to separate and/or detect constituents of interest in a sample, where the sample size is small. For example, the method may be configured to separate and/or detect constituents of interest in a sample, where the sample size is 1 mL or less, such as 750 µL or less, including 500 µL or less, or 250 µL or less, of 100 µL or less, or 75 µL or less, or 50 µL or less, or 40 µL or less, or 30 µL or less, or 20 µL or less, or 10 µL or less, or 5 µL or less, or 1 µL or less. In some instances, the method is configured to separate and/or detect constituents of interest in a sample, where the sample size is 20 µL or less.

In certain embodiments, the method includes concentrating, diluting, or buffer exchanging the sample prior to directing the sample through the separation medium. Concentrating the sample may include contacting the sample with a concentration medium prior to contacting the sample with the separation medium. The concentration medium may include a small pore size polymeric gel, a membrane (e.g., a size exclusion membrane), combinations thereof, and the like. Concentrating the sample prior to contacting the sample with the separation medium may facilitate an increase in the resolution between the bands of analytes in the separated sample because each separated band of analyte may disperse less as the sample traverses through the separation medium. Diluting the sample may include contacting the sample with additional buffer prior to contacting the sample with the separation medium. Buffer exchanging the sample may include contacting the sample with a buffer exchange medium prior to contacting the sample with the separation medium. The buffer exchange medium may include a buffer different from the sample buffer. The buffer exchange medium may include, but is not limited to, a molecular sieve, a porous resin, and the like.

In certain embodiments, the method includes contacting the separated analytes bound to the separation medium with a blocking reagent prior to detecting the analyte of interest. In some cases, contacting the separated analytes with a blocking reagent prior to detecting the analyte of interest may facilitate a minimization in non-specific binding of a detectable label to the separated analytes. For example, contacting the separated analytes with the blocking reagent prior to detecting the analyte of interest may facilitate a minimization in non-specific binding of a labeled antibody to the separated analytes. The blocking reagent can be any blocking reagent that functions as described above, and may include, but is not limited to, bovine serum albumin (BSA), non-fat dry milk, casein, and gelatin. In other embodiments, no blocking step is required. Thus, in these embodiments, the method does not include a blocking step prior to detecting the analyte of interest.

In certain embodiments, the method also includes optional washing steps, which may be performed at various times before, during and after the other steps in the method. For example, a washing step may be performed after binding the separated sample to the separation medium, after contacting the separated sample with the blocking reagent, after contacting the separated sample with the detectable label, etc.

Embodiments of the method may also include releasing the analyte bound to the separation medium. The releasing may include contacting the bound analyte with a releasing agent. The releasing agent may be configured to disrupt the binding interaction between the analyte and the separation medium. In some cases, the releasing agent is a reagent, buffer, or the like, that disrupts the binding interaction between the analyte and the separation medium causing the separation medium to release the analyte. After releasing the analyte from the separation medium, the method may include transferring the analyte away from the separation medium. For example, the method may include directing the released analyte downstream from the separation medium for secondary analysis with a secondary analysis device such as, but is not limited to, a UV spectrometer, and IR spectrometer, a mass spectrometer, an HPLC, an affinity assay device, a second microfluidic device as described herein, and the like.

In some embodiments, the methods include the uniplex analysis of an analyte in a sample. By "uniplex analysis" is meant that a sample is analyzed to detect the presence of one analyte in the sample. For example, a sample may include a mixture of an analyte of interest and other molecular entities that are not of interest. In some cases, the methods include the uniplex analysis of the sample to determine the presence of the analyte of interest in the sample mixture.

Certain embodiments include the multiplex analysis of two or more analytes in a sample. By "multiplex analysis" is meant that the presence two or more distinct analytes, in which the two or more analytes are different from each other, is determined. For example, analytes may include detectable differences in their molecular mass, size, charge (e.g., mass to charge ratio), isoelectric point, and the like. In some instances, the number of analytes is greater than 2, such as 4 or more, 6 or more, 8 or more, etc., up to 20 or more, e.g., 50 or more, including 100 or more, distinct analytes. In certain embodiments, the methods include the multiplex analysis of 2 to 100 distinct analytes, such as 4 to 50 distinct analytes, including 4 to 20 distinct analytes. In certain embodiments, multiplex analysis also includes the use of two or more different detectable labels. The two or more different detectable labels may specifically bind to the same or different analytes. In some cases, the two or more different detectable labels may specifically bind to the same analyte. For instance, the two or more different detectable labels may include different antibodies specific for different epitopes on the same analyte. The use of two or more detectable labels specific for the same analyte may facilitate the detection of the analyte by improving the signal-to-noise ratio. In other cases, the two or more different detectable labels may specifically bind to different analytes. For example, the two or more detectable labels may include different antibodies specific for epitopes on different analytes. The use of two or more detectable labels each specific for different analytes may facilitate the detection of two or more respective analytes in the sample in a single assay.

In certain embodiments, the method is an automated method. As such, the method may include a minimum of user interaction with the devices and systems after introducing the sample into the device. For example, the steps of separating the sample constituents in the separation medium to produce a separated sample and applying the stimulus to the separation medium to covalently bond the constituents to the separation medium may be performed by the device and system at predetermined intervals, such that the user need not manually perform these steps. In some cases, the automated method may facilitate a reduction in the total assay time. For example, embodiments of the method, including the separation and detection of analytes in a sample, may be performed in 240 minutes or less, e.g., 180 minutes or less, 120 minutes or less, such as 90 minutes or less, or 60 minutes or less, or 45 minutes or less, or 30 minutes or less, such as 20 minutes or less, including 15 minutes or less, or 10 minutes or less, or 5 minutes or less, or 2 minutes or less, or 1 minute or less.

Aspects of embodiments of the present disclosure further include methods of making the above polymeric separation medium. In some instances, the methods include positioning a monomeric precursor composition of the polymeric separation medium between a first surface and second surface comprising one or more structural features; irradiating the monomeric precursor composition with light having a wavelength sufficient (e.g., blue light) to initiate polymerization of the precursor composition so as to produce the desired composition. The method may further include removing the second surface comprising the one or more structural features such that the first surface (e.g., the solid support) carries a polymeric separation medium that includes a plurality of microwells as described herein. In certain embodiments, the structural features on the second surface include a plurality of posts. The posts on the second surface may include shapes and sizes that correspond to the desired shapes and sizes of the interior volumes of the microwells. In embodiments that include a plurality of posts on the second surface, a polymeric separation medium may be produced that includes a planar array of microwells. In other embodiments, the structural feature on the second surface may correspond to the shape and size of a central well of a polymeric separation medium that includes a circular arrangement of microwells as described herein. For instance, the second surface may include a structural feature such as a cylinder that includes a plurality of posts extending away from the perimeter of the cylinder. The posts on the perimeter of the cylinder may include shapes and sizes that correspond to the desired shapes and sizes of the interior volumes of the microwells. In some embodiments, the height of the cylinder corresponds to the desired thickness of the polymeric separation medium.

Systems

Aspects of certain embodiments include a system configured to perform methods of the present disclosure. In some instances, the system includes a separation medium as described herein. In certain embodiments, the system includes a buffer. As described herein, the buffer may be a buffer composition that includes the buffer. For example, the buffer composition may be a composition configured to act as a carrier for the buffer, such as a hydrogel that includes the buffer. As such, certain embodiments of the system include a polymeric separation medium as described herein and a hydrogel layer that includes a buffer.

The system may also include a source of electromagnetic radiation (i.e., an electromagnetic radiation source). In some cases, the electromagnetic radiation source is a light source. For example, the light source may include a visible light source, a UV light source, an infrared light source, etc. In some instances, the electromagnetic radiation source includes a light source, such as a UV light source. As described above, the electromagnetic radiation source may be used to apply electromagnetic radiation to the separation medium in the microfluidic device to immobilize (e.g., covalently bond) sample constituents to the separation medium.

In certain embodiments, the system also includes a detector. In some cases, the detector is configured to detect a detectable label. The detector may include any type of detector configured to detect the detectable label used in the assay. As described above, detectable label may be a fluorescent label, colorimetric label, chemiluminescent label, multicolor reagent, enzyme-linked reagent, avidin-streptavidin associated detection reagent, radiolabel, gold particle, magnetic label, etc. In some instances, the detectable label is a fluorescent label. In these instances, the detector may be configured to contact the fluorescent label with electromagnetic radiation (e.g., visible, UV, x-ray, etc.), which excites the fluorescent label and causes the fluorescent label to emit detectable electromagnetic radiation (e.g., visible light, etc.). The emitted electromagnetic radiation may be detected by the detector to determine the presence of the labeled analyte bound to the separation medium.

In some instances, the detector may be configured to detect emissions from a fluorescent label, as described above. In certain cases, the detector includes a photomultiplier tube (PMT), a charge-coupled device (CCD), an intensified charge-coupled device (ICCD), a complementary metal-oxide-semiconductor (CMOS) sensor, a visual colorimetric readout, a photodiode, and the like. The system may be configured to produce an image of the separated cellular components based on a signal obtained from the detector.

Systems of the present disclosure may include various other components as desired. For example, the systems may include fluid handling components, such as microfluidic fluid handling components. The fluid handling components may be configured to direct one or more fluids through the device. In some instances, the fluid handling components are configured to direct fluids, such as, but not limited to, fluid samples, buffers (e.g., electrophoresis buffers, wash buffers, release buffers, etc.), and the like. In certain embodiments, the fluid handling components are configured to deliver a fluid to the separation medium of the device, such that the fluid contacts the separation medium. The fluid handling components may include pumps (e.g., microfluidic pumps). In some cases, the pumps are configured for pressure-driven fluid handling and routing of fluids through the devices and systems disclosed herein. In certain instances, the fluid handling components are microfluidic fluid handling components configured to deliver small volumes of fluid, such as 1 mL or less, such as 500 µL or less, including 100 µL or less, for example 50 µL or less, or 25 µL or less, or 10 µL or less, or 5 µL or less, or 1 µL or less.

In certain embodiments, the systems include one or more electric field generators. An electric field generator may be configured to apply an electric field to various regions of the device, e.g., to the separation medium. The system may be configured to apply an electric field such that the sample is electrokinetically transported through the device. For example, the electric field generator may be configured to apply an electric field to the separation medium. In some cases, the applied electric field may be aligned with the directional axis of the separation medium. As such, the applied electric field may be configured to electrokinetically transport the analytes and components in a sample through the separation medium. In some instances, the electric field generators are configured to apply an electric field with a strength ranging from 10 V/cm to 1000 V/cm, such as from 100 V/cm to 800 V/cm, including from 200 V/cm to 800 V/cm, or from 400 v/cm to 800 V/cm.

In certain embodiments, the system includes an electric field generator configured to apply an electric field such that analytes and/or constituents in the sample are isoelectrically focused in the separation medium. For instance, an applied electric field may be aligned with the directional axis of the separation medium and configured to isoelectrically focus the sample constituents along the directional axis of the separation medium.

In some embodiments, the electric field may be directionally distinct. For example, the electric field may be aligned with the directional axis of the separation medium. The electric field may be configured to direct the sample or analytes through the separation medium along the directional axis of the separation medium.

In certain embodiments, the system includes one or more electric field generators configured to generate an electric field. In certain instances, the electric field generators may be proximal to the device, such as arranged on the device. In some cases, the electric field generators are positioned a distance away from the device. For example, the electric field generators may be incorporated into the system for use with the device.

Utility

The subject devices, systems and methods find use in a variety of different applications where determination of the presence or absence, and/or quantification of one or more analytes in a sample is desired. For example, the subject devices, systems and methods find use in the separation and detection of proteins, peptides, nucleic acids, and the like, which may be present in a cell or a sub-cellular compartment. In some cases, the subject devices, systems and methods find use in the separation and detection of cellular proteins. For example, the subject devices, systems and methods find use in the detection of proteins associated with the development of cancer treatments, for development of stem cell therapy, for high-throughput drug screening, for biological analyses regarding human aging, and the like.

The subject devices, systems and methods find use in development and validation of stem cell de-differentiation and differentiation protocols. For instance, induced pluripotent stem cells may be derived from somatic cells such as skin cells, which may involve reprogramming of somatic cells with various external stimuli (e.g., chemical or biological stimuli) to induce the cells to a pluripotent state. In some instances, when experimenting with new external stimuli to achieve pluripotency, it may be desirable to measure the response of the cell population to determine if pluripotency has been achieved. The subject devices, systems and methods find use in measuring these responses of the cell population to determine if pluripotency has been achieved. For example, the subject devices, systems and methods find use in measuring multiple protein targets that are known pluripotency indicators such as, but not limited to, Oct-3/4, Nanog, SSEA-4, and SOX2. The subject devices, systems and methods find use in determining the heterogeneity of the transformed cell population to determine the percentage of the cells that have been successfully transformed to a pluripotent state. Such induced pluripotent stem cells can then be differentiated via external chemical or biological stimuli to derive various cell types such as, but not limited to, cardiomyocytes, neurons, hepatocytes and endothelial cells. The subject devices, systems and methods find use in the validation of such differentiation protocols because, in certain embodiments, subject devices, systems and methods can simultaneously detect multiple protein markers that are indicative of successful differentiation to the target cell type. The subject devices, systems and methods find use in determining the heterogeneity of the transformed cell population to determine the percentage of the cells that have successfully differentiated to the target cell type.

The subject devices, systems and methods also find use in development and validation of "disease-in-a-dish" models. For example, it may be challenging for researchers to study diseases in the human brain since extracting neurons from living patients is difficult and risky. As an alternative, cellular models of disease may be created to allow basic scientific research and drug development. Such models can be created, for example, by differentiation of neurons from induced pluripotent stem cells (IPSCs) derived from skin cells donated by patients with a genetic neurodegenerative disease. To create these models, stem cell differentiation protocols may be developed and validated as previously described to de-differentiate skin cells to stem cells and then differentiate the stem cells to neurons. Once this transformation is successful, the model may be validated by determining that characteristics of the disease are present in the differentiated cells. For example, neurons can be created from the skin cells of patients with Huntington's disease. Once created, the derived cells may be tested for expression of the diseased form of the Huntingtin protein. The subject devices, systems and methods find use in detecting the presence and heterogeneity of the Huntingtin protein in the disease model and verifying similarity to primary cells. Disease-in-a-dish models may also be created through selection or genetic modification of cell lines. Such cells may be validated to ensure that the genetic modification results in stable expression of a diseased biomarker (e.g., a protein) that mimics what is seen in diseased primary cells. The subject devices, systems and methods find use in creating disease models of the liver, kidney, heart, brain, blood or other organs, tissues and cell types.

The subject devices, systems and methods also find use in measuring the heterogeneity of cancerous tumors. Specific biomarkers such as, for example, HER-2 and BRAF, are indicative of certain cancer mutations and are targets for drugs such as trastuzumab and vemurafenib, respectively. Cancer may be a highly heterogeneous disease and targets such as HER-2 and BRAF may not be expressed uniformly within a tumor. Such heterogeneity may have implications for clinical diagnosis and treatment. The subject devices, systems and methods find use in analyzing the heterogeneity of multiple targets in a cell population derived from a tumor biopsy. Such an approach may facilitate basic scientific research, drug discovery and development, and companion diagnostics for targeted therapeutics.

The subject devices, systems and methods also find use in the determination of the mechanism of action of drug compounds. For example, "disease-in-a-dish" models may be used as in vitro test platforms for drug development. Drugs can be developed to target specific targets and pathways that are present in both the disease and disease models. The subject devices, systems and methods find use in analyzing the heterogeneous response of a cell population after exposure to a drug candidate. Response to the drug can be correlated to the presence of the primary target and heterogeneous responses within the cell population not explained by the presence or absence of the primary target can be further correlated with other proteins and signaling pathways. In this way, the subject devices, systems and methods find use in determining the mechanism of action of the drug, which may facilitate more efficient research, development and eventual approval of the drug compound.

The subject devices, systems and methods also find use in the analysis of circulating tumor cells (CTCs) isolated from blood. CTCs are cancerous cells in circulation that are shed from primary tumors and may be used for early cancer diagnosis, prognosis, monitoring of treatment, detection of metastases, or other uses. Since the CTCs are heterogeneous, each individual cell may be tested for protein biomarkers that are indicative of invasiveness, proliferation, or other factors. Typical methods for enriching CTCs from whole blood yield a suspension of cells enriched in the target CTCs. The subject devices, systems and methods find use in analyzing such a cell suspension, for example using methods utilizing active settling of the cells to maximize the number of cells in the input suspension that are captured and analyzed. Analysis of CTCs by the subject devices, systems and methods find use for basic scientific research, management of minimum residual disease, and cancer diagnosis. In certain instances, active settling includes positioning the sample constituents in one or more microwells using one or more or the following: applying an electric field to the sample; applying a density gradient, physically positioning the sample constituents into the microwell using a positioning device, such as but not limited to a micropipetter, a nozzle, optical tweezers, and the like; applying a pressure force; applying a magnetic force (e.g., where the sample constituents of interest are bound to magnetic beads); convection flow; size selected settling using different sized microwells; positioning droplets of sample containing cells or cell lysates into microwells; combinations thereof and the like.

The subject devices, systems and methods also find use in analysis downstream of fluorescence activated cell sorting (FACS). FACS can sort millions of cells and isolate subpopulations as small as a few hundred cells. However, further analysis of such small subpopulations by flow cytometers may not be suitable because typical flow cytometers require a minimum of 10,000 or more cells. The subject devices, systems and methods find use in analyzing such small cell subpopulations, for example using methods utilizing active settling or placement of the cells to maximize the number of cells in the input suspension that are captured and analyzed. The subject devices, systems and methods find use in the further analysis of the subpopulation for protein targets that include targets in the FACS sort as well as targets that were not part of the FACS sort. For example, primary cells derived from cancerous human or animal tissue can be sorted by FACS to isolate a subpopulation of cells that are putative cancer cells based on one or more surface markers. The subject devices, systems and methods can then be used to confirm the presence of the one or more surface markers and assay for additional targets such as, for example, intracellular proteins and transcription factors that will further characterize the state and heterogeneous composition of the isolated subpopulation.

The subject devices, systems and methods find use in the detection of nucleic acids, proteins, or other biomolecules in a sample. The methods may include the detection of a set of biomarkers, e.g., two or more distinct protein biomarkers, in a sample. For example, the methods may be used in the rapid, clinical detection of two or more disease biomarkers in a biological sample, e.g., as may be employed in the diagnosis of a disease condition in a subject, or in the ongoing management or treatment of a disease condition in a subject, etc. In addition, the subject devices, systems and methods may find use in protocols for the detection of an analyte in a sample, such as, but not limited to, Western blotting, and the like.

The subject devices, systems and methods find use in detecting biomarkers. In some cases, the subject devices, systems and methods may be used to detect the presence or absence of particular biomarkers, as well as an increase or decrease in the concentration of particular biomarkers in blood, plasma, serum, or other bodily fluids or excretions, such as but not limited to urine, blood, serum, plasma, saliva, semen, prostatic fluid, nipple aspirate fluid, lachrymal fluid, perspiration, feces, cheek swabs, cerebrospinal fluid, cell lysate samples, amniotic fluid, gastrointestinal fluid, biopsy tissue, and the like.

The presence or absence of a biomarker or significant changes in the concentration of a biomarker can be used to diagnose disease risk, presence of disease in an individual, or to tailor treatments for the disease in an individual. For example, the presence of a particular biomarker or panel of biomarkers may influence the choices of drug treatment or administration regimes given to an individual. In evaluating potential drug therapies, a biomarker may be used as a surrogate for a natural endpoint such as survival or irreversible morbidity. If a treatment alters the biomarker, which has a direct connection to improved health, the biomarker can serve as a surrogate endpoint for evaluating the clinical benefit of a particular treatment or administration regime. Thus, personalized diagnosis and treatment based on the particular biomarkers or panel of biomarkers detected in an individual are facilitated by the subject devices, systems and methods. Furthermore, the early detection of biomarkers associated with diseases is facilitated by the high sensitivity of the subject devices and systems, as described above. Due to the capability of detecting multiple biomarkers on a single chip, combined with sensitivity, scalability, and ease of use, the presently disclosed microfluidic devices, systems and methods find use in portable and point-of-care or near-patient molecular diagnostics.

The subject devices, systems and methods find use in detecting biomarkers for a disease or disease state. In certain instances, the subject devices, systems and methods find use in detecting biomarkers for the characterization of cell signaling pathways and intracellular communication for drug discovery and vaccine development. For example, the subject devices, systems and methods may be used to detect and/or quantify the amount of biomarkers in diseased, healthy or benign samples. In certain embodiments, the subject devices, systems and methods find use in detecting biomarkers for an infectious disease or disease state. In some cases, the biomarkers can be molecular biomarkers, such as but not limited to proteins, nucleic acids, carbohydrates, small molecules, and the like.

The subject devices, systems and methods find use in diagnostic assays, such as, but not limited to, the following: detecting and/or quantifying biomarkers, as described above; screening assays, where samples are tested at regular intervals for asymptomatic subjects; prognostic assays, where the presence and/or quantity of a biomarker is used to predict a likely disease course; stratification assays, where a subject's response to different drug treatments can be predicted; efficacy assays, where the efficacy of a drug treatment is monitored; and the like. For example, one or more biomarkers may be detected and monitored over an extended period of time, such as over several days, several weeks or several years. Changes in the presence and/or quantity of the one or more biomarkers may be monitored over an extended period of time.

The subject devices, systems and methods also find use in validation assays. For example, validation assays may be used to validate or confirm that a potential disease biomarker is a reliable indicator of the presence or absence of a disease across a variety of individuals. The short assay times for the subject devices, systems and methods may facilitate an increase in the throughput for screening a plurality of samples in a minimum amount of time. For example, the subject devices, systems and methods find use in probed IEF separation medium for affinity reagent screening. High-throughput microfluidic devices that include a separation medium as described herein may be used to select biomarker isoform-specific affinity reagents, such as specific monoclonal antibodies. Such reagents may be used in ELISA assays for disease-specific biomarker isoforms present in clinical proteinaceous samples. In some cases, reagents may be screened in serial or for their multiplexed (parallel) capability for highly specific binding.

The subject devices, systems and methods also find use in a variety of different applications where separation of one or more constituents (e.g., analytes) in a sample is desired. The constituents in the sample may be separated based on a variety of different separation techniques, such as, but not limited to, electrochromotography, electrophoretic immunoassays, equilibrium separations (including isoelectric and temperature gradient focusing), micellar electrokinetic chromatography, chromatography variants, native electrophoresis, and separation by protein mass under denaturing conditions (e.g., SDS-PAGE). Any of the separation techniques may be coupled to subsequent analyte probing by, for example, antibodies (or variants), lectins, substrates, ligands, lipids, coated particles or dyes. For example, separation based on protein sizing with subsequent antibody probing provides an integrated microfluidic Western blotting device.

In some instances, the subject devices, systems and methods can be used without requiring a laboratory setting for implementation. In comparison to the equivalent analytic research laboratory equipment, the subject devices and systems provide comparable analytic sensitivity in a portable, hand-held system. In some cases, the mass and operating cost are less than the typical stationary laboratory equipment. The subject systems and devices may be integrated into a single apparatus, such that all the steps of the assay, including separation, transfer, labeling and detecting of an analyte of interest, may be performed by a single apparatus. For example, in some instances, there are no separate apparatuses for separation, transfer, labeling and detecting of an analyte of interest. In addition, the subject systems and devices can be utilized in a home setting for over-the-counter home testing by a person without medical training to detect one or more analytes in samples. The subject systems and devices may also be utilized in a clinical setting, e.g., at the bedside, for rapid diagnosis or in a setting where stationary research laboratory equipment is not provided due to cost or other reasons.

Kits

Aspects of embodiments of the present disclosure further include kits configured for use in the methods described herein. In some instances, the kits include a device as described herein, such as a device that includes a polymeric separation medium having a plurality of microwells. In certain embodiments, the kit may include a packaging configured to contain the device. The packaging may be a sealed packaging, such as a sterile sealed packaging. By "sterile" is meant that there are substantially no microbes (such as fungi, bacteria, viruses, spore forms, etc.). In some instances, the packaging may be configured to be sealed, e.g., a water vapor-resistant packaging, optionally under an air-tight and/or vacuum seal.

Aspects of the present disclosure additionally include kits that further include a buffer. For instance, the kit may include a buffer, such as an electrophoresis buffer, a sample buffer, and the like. In certain cases, the buffer is an electrophoresis buffer, such as, but not limited to, a Tris buffer, a Tris-glycine, and the like. In some instances, the buffer includes a detergent (such as sodium dodecyl sulfate, SDS).

The kits may further include additional reagents, such as but not limited to, release reagents, denaturing reagents, refolding reagents, detergents, detectable labels (e.g., fluorescent labels, colorimetric labels, chemiluminescent labels, multicolor reagents, enzyme-linked reagents, detection reagents (e.g., avidin-streptavidin associated detection reagents), e.g., in the form of at least one if not more analyte detection reagents (such as first and second analyte detection reagents), calibration standards, radiolabels, gold particles, magnetic labels, etc.), and the like.

In certain embodiments, the kit may include an analyte detection reagent, such as a detectable label, as described herein. The detectable label may be associated with a member of a specific binding pair. Suitable specific binding pairs include, but are not limited to: a member of a receptor/ligand pair; a ligand-binding portion of a receptor; a member of an antibody/antigen pair; an antigen-binding fragment of an antibody; a hapten; a member of a lectin/carbohydrate pair; a member of an enzyme/substrate pair; biotin/avidin; biotin/streptavidin; digoxin/antidigoxin; a member of a DNA or RNA aptamer binding pair; a member of a peptide aptamer binding pair; and the like. In certain embodiments, the member of the specific binding pair includes an antibody. The antibody may specifically bind to an analyte of interest in the separated sample bound to the separation medium. For example, the detectable label may include a labeled antibody (e.g., a fluorescently labeled antibody) that specifically binds to the analyte of interest.

In addition to the above components, the subject kits may further include instructions for practicing the subject methods. These instructions may be present in the subject kits in a variety of forms, one or more of which may be present in the kit. One form in which these instructions may be present is as printed information on a suitable medium, e.g., a piece or pieces of paper on which the information is printed, in the packaging of the kit, in a package insert, etc. Another means would be a computer readable medium, e.g., CD, DVD, Blu-Ray, computer-readable memory, etc., on which the information has been recorded or stored. Yet another means that may be present is a website address which may be used via the Internet to access the information at a removed site. Any convenient means may be present in the kits.

As can be appreciated from the disclosure provided above, embodiments of the present invention have a wide variety of applications. Accordingly, the examples presented herein are offered for illustration purposes and are not intended to be construed as a limitation on the invention in any way. Those of ordinary skill in the art will readily recognize a variety of noncritical parameters that could be changed or modified to yield essentially similar results. Thus, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by mass, molecular mass is mass average molecular mass, temperature is in degrees Celsius, and pressure is at or near atmospheric.

EXAMPLES

Example 1

Embodiments included a single-cell Western blot for analyses of sub-cellular compartments (e.g., cytosol, nucleus). Protein sub-cellular localization is intrinsically linked to function, with aberrant localization linked to numerous diseases. Existing sub-cellular protein analyses are slow, offer low multiplexing (~5 proteins), and are not quantitative. Single-cell Western blotting arrays (scWesterns) included a capacity to (1) differentially lyse specific sub-cellular compartments in single cells, (2) perform single-cell Western blotting solely on proteins in those targeted compartments (5+ proteins per compartment), and (3) serially assay multiple sub-cellular compartments in the same single-cells. The specificity of scWesterns with sub-cellular resolution was used to study of intracellular signaling pathways, which may facilitate the analysis of life processes that are difficult to measure.

The sub-cellular scWesterns provided selectivity by using a buffer system for serial lysis and analysis of specific sub-cellular compartments. The multifunctional buffer system was compatible with both compartment-specific lysis and subsequent electrophoresis. The scWestern included a microscope slide coated with a thin photoactive polyacrylamide gel stippled with thousands of microwells. Cells were gravity-settled into microwells and, after chemical lysis and application of electric field, gel contiguous to the microwells supported protein electrophoresis of cell lysate, then acted a scaffold for photo-capture of separated proteins for subsequent antibody probing.

A polyacrylamide microwell array was fabricated on top of a functionalized glass microscope slide (30 µm thick, 30 µm diameter microwells). In parallel, a 40×50×0.5 mm 15% T polyacrylamide lid was fabricated and soaked in a cytosol lysis buffer (digitonin, Triton X-100, tris-glycine). Next, GFP-expressing U373 cells in a PBS suspension were added into the microwell. The cell suspension was sufficiently diluted and the microwells were dimensioned such that most occupied wells contained only one cell. The cytosolic lysis buffer-soaked lid was applied for 30 seconds. After cytosolic lysis, the electric field (40 V/cm) was applied for 15 seconds. During electrophoresis, the GFP was imaged through an inverted epifluorescent microscope.

Figure 2:
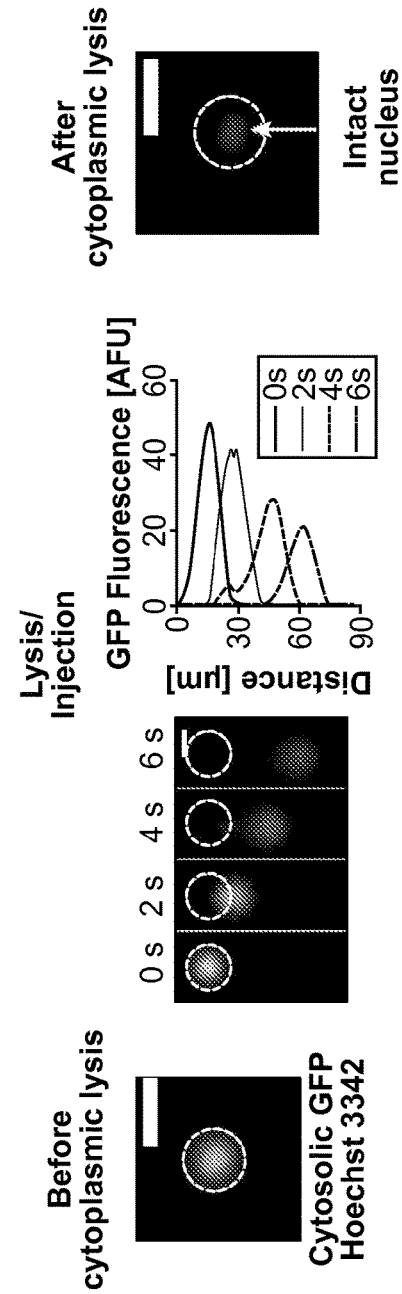
FIG. 2 shows images of an assay where multifunctional buffers preferentially solubilized cytosolic glioblastoma cell fraction (GFP) and supported polyacrylamide gel electrophoresis of that fraction, according to embodiments of the present disclosure. Nucleus remained intact throughout the assay (Hoechst DNA stain).

As described above, to achieve timed delivery of the lysis buffer sequence to the microarray, a thick buffer-infused hydrogel layer (e.g., "lysis lid") was used. Upon contact with a "lysis lid", the lysis buffer diffused into the microwell array, lysing all cells nearly simultaneously. FIG. 2 shows that the multifunctional buffer system enabled rapid cytosol-specific lysis (60s) with the nucleus retained intact in the microwell (assessed by a Hoechst 3342 stain). FIG. 2 shows successful electrophoretic injection of cytosolic GFP from U373 glioblastoma cells into the hydrogel for subsequent Western blotting.

Example 2

A polyacrylamide microwell array was fabricated on top of a functionalized glass microscope slide (30 µm thick, 30 µm diameter microwells). Next, GFP-expressing U373 cells in a PBS suspension were added into the microwell. The cell suspension was sufficiently diluted and the microwells were dimensioned such that most occupied wells contained only one cell. A cytosolic lysis buffer-soaked lid containing digitonin, Triton X-100, and tris-glycine was applied for 30 seconds. After cytosolic lysis, the electric field (40 V/cm) was applied for 15 seconds and the proteins were photocaptured to the polyacrylamide gel. Next, a nuclear lysis buffer-soaked lid (SDS, sodium deoxycholate, Triton X-100, tris-glycine) was applied for 30 seconds. After nuclear lysis, an electric field (40 V/cm) was applied in the opposite direction to the electric field applied for the cytosolic lysis separation for 25 seconds, and then the nuclear proteins were photo-captured to the polyacrylamide gel. Next, the slides were probed for Lamin A/C (1:10 primary antibody dilution, 1:30 AF647-labeled secondary antibody dilution). Slides were imaged with a microarray scanner and protein expression and distribution (cytosol vs. nucleus) were quantified with a custom MATLAB script.

Figures 3A, 3B:
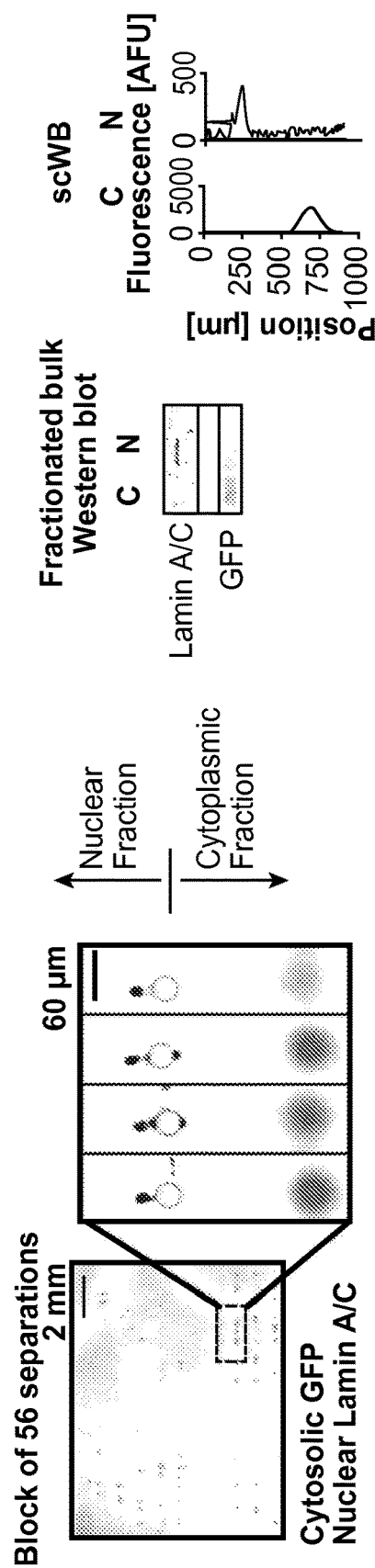
FIGS. 3A and 3B show images and graphs of a sub-cellular single-cell Western assay according to embodiments of the present disclosure. The results indicated successfully resolved proteins in cytoplasmic and nuclear fractions.

As described above, microarray format was used to perform sequential Western blotting along two axes—for increasing data density by spatially separating cytosolic from nuclear proteins. FIG. 3A shows bidirectional sub-cellular scWestern for 92 single glioblastoma cells (U373, GFP-expressing). To validate fractionation of the gliobastoma cells into separate cytoplasmic and nuclear fractions, a cytoplasm-specific protein (GFP) and a nuclear-specific protein (Lamin A/C) were probed after differential lysis and electrophoresis on the scWestern. Correct localization of Lamin A/C (92%, n=92 cells) and GFP (100%, n=92 cells) was observed, which agreeded well with conventional bulk Western blots (FIG. 3B).

The results showed that single-cell protein analysis was performed using a single-cell Western blot for analyses of proteins localized to specific sub-cellular compartments. The scWesterns find use in studying dynamic processes, including sub-cellular protein translocation, a fundamental aspect of cellular response and regulation.

Example 3

The technical variance in the Subcellular Western blotting assay was assessed by comparing sequential measurements of the same cell type. The distribution of NF-KB localization using three nonparametric measures was compared: median, skew, and interquartile range. The technical variance to immunocytochemistry was compared (FIG. 4, panels A-C).

A polyacrylamide microwell array was fabricated on top of a functionalized glass microscope slide (40 μm thick, 32 μm diameter microwells). Next, U373 cells in a PBS suspension were settled into the microwell. The cell suspension was sufficiently diluted and the microwells were dimensioned such that most occupied wells contained only one cell. The cell suspension was divided across three different devices. A cytosolic lysis buffer-soaked lid containing digitonin, Triton X-100, and tris-glycine was applied for 25 seconds. After cytosolic lysis, the electric field (100 V/cm) was applied for 35 seconds and the protein was photocaptured to the polyacrylamide gel. Next, a nuclear lysis buffer-soaked lid (SDS, sodium deoxycholate, Triton X-100, tris-glycine, heated to 50° C.) was applied for 25 seconds. After nuclear lysis, an electric field (66.67 V/cm) was applied in the opposite direction to the electric field applied for the cytosolic lysis separation for 11 seconds and then the nuclear proteins were photocaptured to the polyacrylamide gel. All three devices were probed for NF-KappaB (1:25 primary antibody dilution, 1:30 AF647-labeled secondary antibody dilution). Protein expression was quantified with a custom MATLAB script. Localization (nuclear NF-KappaB/total NF-KappaB) distributions were compared using three nonparametric estimators: median, interquartile range, and metric skew.

In parallel, 4 samples of U373 cells were stained for NF-KappaB using immunocytochemistry. The cells were fixed with 4° C. 4% paraformaldehyde for 15 minutes. Then, the cells were blocked with 5% donkey serum in tris-buffered saline with Tween 20. The cells were stained with the same antibodies as the subcellular Western blot samples (1:300 primary antibody dilution, 1:300 secondary antibody dilution) and then the nuclei were stained with Hoechst 33342. The stained cells were imaged with an inverted epifluorescent microscope and the protein expression was quantified with Cell Profiler. The distributions were characterized in the same manner as the subcellular Western blot samples.

Figure 4:
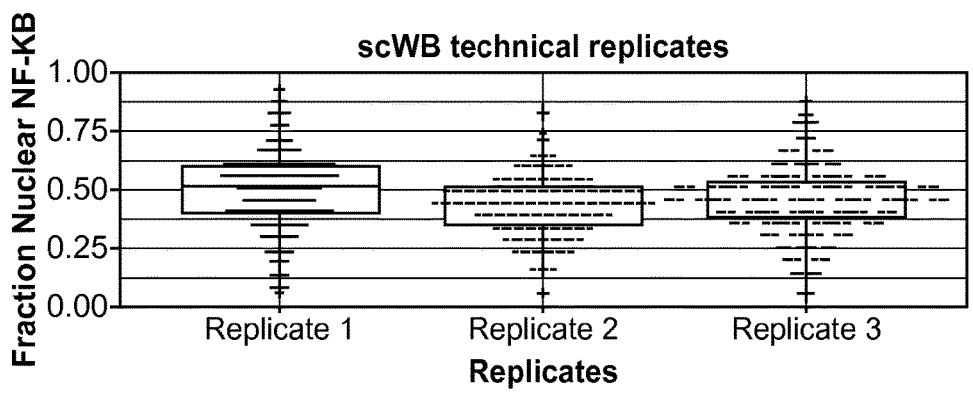
FIG. 4, panels A-C, show graphs of the technical variance characterization of DDF single-cell Western blots (scWB), according to embodiments of the present disclosure. Boxplots of nuclear NF-KB fraction in un-stimulated U373 cells were measured by scWB (FIG. 4, panel A) and immunocytochemistry (ICC.
Figure 4:
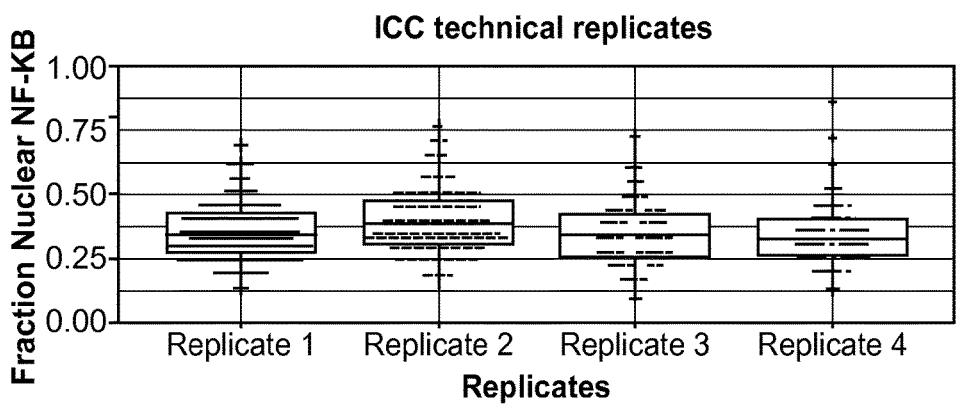
Figure 4:
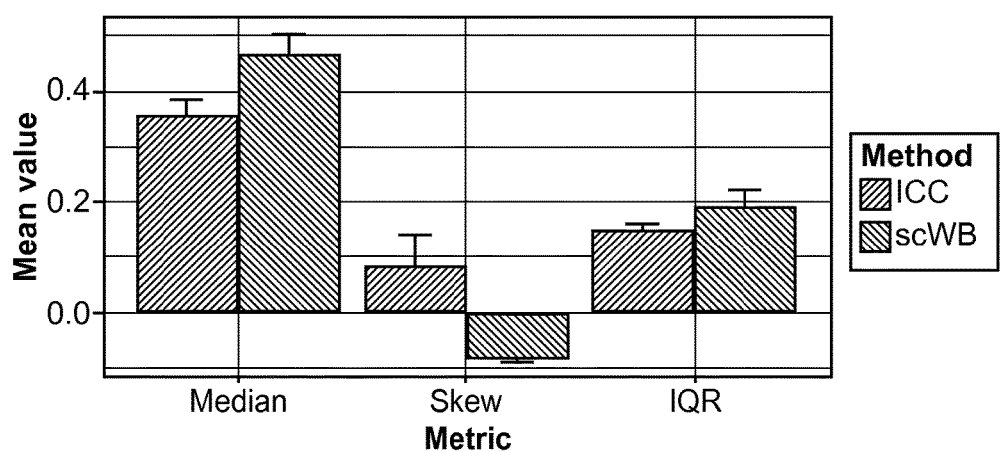

FIG. 4, panels A-C, show graphs of the technical variance characterization of DDF single-cell Western blots (scWB), according to embodiments of the present disclosure. Box-plots of nuclear NF-KB fraction in un-stimulated U373 cells were measured by scWB (FIG. 4, panel A) and immunocytochemistry (ICC; FIG. 4, panel B). FIG. 4, panel C shows a graph of a comparison of nonparametric parameters (mean+/−SD).

Example 4

A translocation assay using U373 human glioblastoma cells was performed. The U373 cells were stimulated with 5 pg/mL lipopolysaccharides for varying time of (0, 15, 30, 45, 60, 90, and 120 minutes) and the distribution of (cytosol vs. nucleus) of NF-KB was measured. After stimulation, the cells were assayed for NF-KappaB expression by the subcellular Western blot using the same methods as described in Example 3. In parallel, cells stimulated by the same lipopolysaccharide preparations were assayed for NF-KappaB expression using the same immunocytochemistry methods as described in Example 3. Similar changes in NF-KB localizations were observed using the subcellular Western blot as with ICC (FIG. 5, panels A-C).

Figure 5:
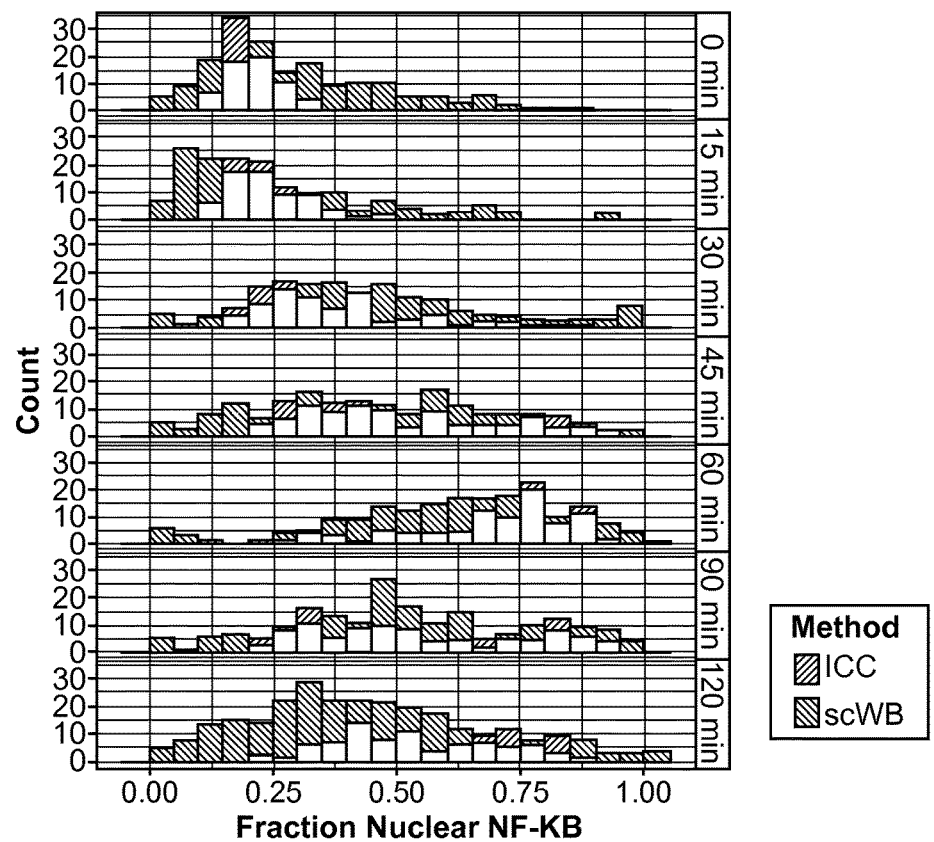
FIG. 5, panels A-C, show graphs of subcellular Western Blots used to measure dynamic changes in protein localization. U373 cells were stimulated with 5 microgram/mL lipopolysaccharides for the indicated times.
Figure 5:
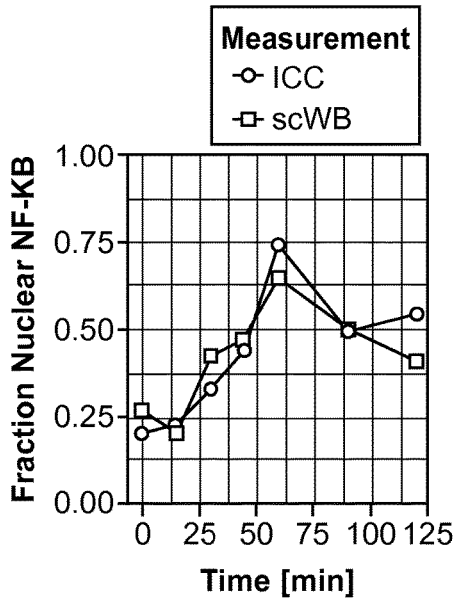
Figure 5:
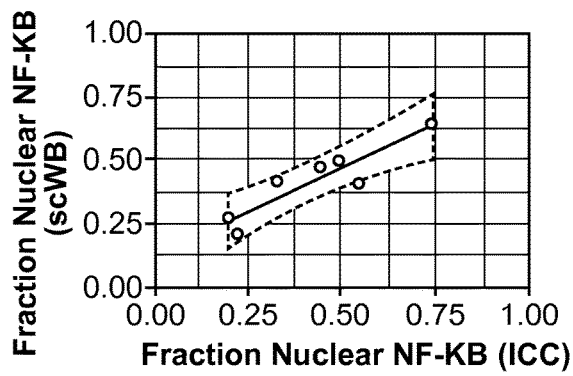

FIG. 5, panels A-C, show graphs of subcellular Western Blots used to measure dynamic changes in protein localization. U373 cells were stimulated with 5 microgram/mL lipopolysaccharides for the indicated times. FIG. 5, panel A, shows histograms of nuclear NF-KappaB expression. FIG. 5, panel B, shows a scatter plot of median NF-KB localization during the translocation assay. FIG. 5, panel C, shows the Pearson correlation coefficient of the medians of ICC and subcellular Western blotting measurements during the translocation assay (rho=0.90).

Although the foregoing embodiments have been described in some detail by way of illustration and example for purposes of clarity of understanding, it is readily apparent to those of ordinary skill in the art in light of the teachings of the present disclosure that certain changes and modifications may be made thereto without departing from the spirit or scope of the appended claims. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A method of detecting an analyte, the method comprising:
   (a) contacting a sample comprising a cell with a polymeric separation medium comprising a microwell, wherein the polymeric separation medium comprises functional groups that covalently bond one or more cellular components to the polymeric separation medium upon application of an applied stimulus;
   (b) contacting the polymeric separation medium with a first buffer sufficient to differentially lyse a first sub-cellular compartment of the cell to produce a first set of cellular components;
   (c) applying an electric field to the polymeric separation medium in a manner sufficient to move at least some of the first set of cellular components into the polymeric separation medium to produce a first set of separated cellular components in the polymeric separation medium;
   (d) immobilizing the first set of separated cellular components in the polymeric separation medium; and
   (e) contacting the polymeric separation medium with a second buffer sufficient to differentially lyse a second sub-cellular compartment of the cell to produce a second set of cellular components.

2. The method of claim 1, wherein the contacting (a) is sufficient to position the cell in the microwell.

3. The method of claim 1, wherein the contacting (b) comprises contacting a surface of the polymeric separation medium with a hydrogel layer comprising the first buffer.

4. The method of claim 1, wherein the first buffer is sufficient for the contacting (b) and the applying (c).

5. The method of claim 1, wherein the immobilizing comprises covalently bonding the first set of separated cellular components to the polymeric separation medium.

6. The method of claim 1, further comprising applying an electric field to the polymeric separation medium in a manner sufficient to move at least some of the second set of cellular components into the polymeric separation medium to produce a second set of separated cellular components in the polymeric separation medium.

7. The method of claim 6, wherein the second set of cellular components is separated in a direction different from the first set of cellular components.

8. The method of claim 6, further comprising immobilizing the second set of separated cellular components in the polymeric separation medium.

9. The method of claim 1, further comprising detecting the separated cellular components.

10. The method of claim 9, wherein the detecting comprises contacting the separated cellular components with an analyte detection reagent.

11. The method of claim 10, further comprising contacting the separated cellular components with one or more secondary reagents.

12. The method of claim 1, further comprising imaging the polymeric separation medium to produce an image of the separated cellular components.

13. The method of claim 1, wherein the functional groups are co-polymerized with the polymeric separation medium.

14. A system for detecting an analyte, the system comprising:
   a polymeric separation medium comprising a microwell, wherein the polymeric separation medium comprises functional groups that covalently bond one or more cellular components to the polymeric separation medium upon application of an applied stimulus;
   a first hydrogel layer comprising a first buffer sufficient to differentially lyse a first sub-cellular compartment of a cell to produce a first set of cellular components in the microwell; and
   a second hydrogel layer comprising a second buffer sufficient to differentially lyse a second sub-cellular compartment of the cell to produce a second set of cellular components in the microwell.

15. The system of claim 14, wherein the first hydrogel layer is positioned on a surface of the polymeric separation medium such that the first buffer is in fluid communication with the microwell.

16. The system of claim 14, wherein the microwell is dimensioned to accommodate a single cell.

17. The system of claim 14, wherein the polymeric separation medium comprises an array of microwells in the polymeric separation medium.

18. The system of claim 14, wherein the polymeric separation medium comprises 100 or more microwells.

19. A kit comprising:
   a polymeric separation medium comprising a microwell, wherein the polymeric separation medium comprises functional groups that covalently bond one or more cellular components to the polymeric separation medium upon application of an applied stimulus:
   a hydrogel;
   a first buffer sufficient to differentially lyse a first sub-cellular compartment of a cell to produce a first set of cellular components in the microwell;
   a second buffer sufficient to differentially lyse a second sub-cellular compartment of the cell to produce a second set of cellular components in the microwell; and
   a packaging containing the system.

* * * * *